US007825236B2

(12) United States Patent
Renzi et al.

(10) Patent No.: US 7,825,236 B2
(45) Date of Patent: Nov. 2, 2010

(54) OLIGONUCLEOTIDE COMPOSITIONS AND METHODS FOR TREATING DISEASE INCLUDING INFLAMMATORY CONDITIONS

(75) Inventors: Paolo Renzi, Westmount (CA); Khalid Zemzoumi, Montreal (CA); Helene D'Anjou, Brossard (CA)

(73) Assignee: Topigen Pharmaceutique Inc. (CA)

( * ) Notice: Subject to any disclaimer, the term of this patent is extended or adjusted under 35 U.S.C. 154(b) by 0 days.

(21) Appl. No.: 12/187,433

(22) Filed: Aug. 7, 2008

(65) Prior Publication Data

US 2009/0029938 A1 Jan. 29, 2009

Related U.S. Application Data

(62) Division of application No. 10/953,512, filed on Sep. 29, 2004, now Pat. No. 7,579,455.

(60) Provisional application No. 60/507,016, filed on Sep. 29, 2003.

(51) Int. Cl.
C07H 21/04 (2006.01)
(52) U.S. Cl. .................. 536/24.5; 536/24.31; 536/24.1; 435/6; 435/325; 435/375; 514/44
(58) Field of Classification Search ........................ None
See application file for complete search history.

(56) References Cited

U.S. PATENT DOCUMENTS

| | | | |
|---|---|---|---|
| 4,880,635 A | 11/1989 | Janoff et al. | |
| 4,906,477 A | 3/1990 | Kurono et al. | |
| 4,911,928 A | 3/1990 | Wallach | |
| 4,917,951 A | 4/1990 | Wallach | |
| 4,920,016 A | 4/1990 | Allen et al. | |
| 4,921,757 A | 5/1990 | Wheatley et al. | |
| 5,734,039 A | 3/1998 | Calabretta et al. | |
| 5,885,834 A | 3/1999 | Epstein | |
| 6,165,789 A | 12/2000 | Monia et al. | |
| 6,348,450 B1 | 2/2002 | Tang et al. | |
| 7,022,849 B2 | 4/2006 | Pitts et al. | |
| 2003/0045490 A1* | 3/2003 | Dale et al. | 514/44 |
| 2003/0220273 A1 | 11/2003 | Bennett et al. | |

FOREIGN PATENT DOCUMENTS

| | | |
|---|---|---|
| WO | 97/35989 | 10/1997 |
| WO | 99/66037 A2 | 12/1999 |
| WO | 00/40714 A2 | 7/2000 |
| WO | 02/22661 A2 | 3/2002 |
| WO | 03/012030 A2 | 2/2003 |

OTHER PUBLICATIONS

Essayan, DM, "Cyclic Nucleotide Phosphodiesterase (PDE) Inhibitors and and Immunomodulation." Biochemical Pharmacology 57:965-973, 1999.

Perry, MJ and Higgs, GA, "Chemotherapeutic potential of phosphodiesterase inhibitors." Current Opinion in Chemical Biology 2:472-481, 1998.

Bundschuh, DS et al., "In Vivo Efficacy in Airway Disease Models of Roflumilast, a Novel Orally Active PDE4 Inhibitor." The Journal of Pharmacology and Experimental Therapeutics 297(1):280-290, 2001.

Burnouf, C and Pruniaux, M-P, "Recent Advances in PDE4 Inhibitors as Immunoregulators and Anti-Inflammatory Drugs." Current Pharmaceutical Design 8:1255-1296, 2002.

Giembycz, MA, "Cilomilast: a second generation phosphodiesterase 4 inhibitor for asthma and chronic obstructive pulmonary disease." Expert Opin Investig Drugs 10(7):1361-1379, 2001.

Torphy, TJ, "Phosphodiesterase Isozymes." Am J Respir Crit Care Med 157:351-370, 1998.

Au, B-T et al., "Effect of PDE4 inhibitors on zymosan-induced IL-8 release from human neutrophils: synergism with prostanoids and salbutamol." British Journal of Pharmacology 123:1260-1266, 1998.

Compton, CH et al., "Cilomilast, a selective phosphodiesterase-4 inhibitor for treatment of patients with chronic obstructive pulmonary disease: a randomised, dose-ranging study." The Lancet 358:265-270, 2001.

Ma, D et al., "Phosphodiesterase 4B Gene Transcription Is Activated by Lipopolysaccharide and Inhibited by Interleukin-10 in Human Monocytes." Molecular Pharmacology 55:50-57, 1999.

Wang, P et al., "Phosphodiesterase 4B2 Is the Predominant Phosphodiesterase Species and Undergoes Differential Regulation of Gene Expression in Human Monocytes and Neutrophils." Molecular Pharmacology 56:170-174, 1999.

Churg, A et al., "Acute Cigarette Smoke-Induced Connective Tissue Breakdown Requires both Neutrophils and Macrophage Metalloelastase in Mice." Am J Respir Cell Mol Biol 27:368-374, 2002.

Churg, A et al., "Tumor Necrosis Factor-alpha Is Central to Acute Cigarette Smoke-induced Inflammation and Connective Tissue Breakdown." Am J Respir Crit Care Med 166:849-854, 2002.

Gaede, Ki et al., "Analysis of differentially regulated mRNAs in monocytic cells induced by in vitro stimulation." J Mol Med 77:847-852, 1999.

Kebelmann-Betzing, C et al., "Charaterization of Cytokine, Growth Factor Receptor, Costimulatory and Adhesion Molecule Expression Patterns of Bone Marrow Blasts in Relapsed Childhood B Cell Precursor All." Cytokine 13 (1):39-50, 2001.

(Continued)

Primary Examiner—Kimberly Chong
(74) Attorney, Agent, or Firm—Nixon Peabody LLP

(57) ABSTRACT

The invention relates to therapeutic antisense oligonucleotides directed against genes coding for phosphodiesterase (PDEs) and the use of these in combination. These antisense oligonucleotides may be used as analytical tools and/or as therapeutic agents in the treatment of disease associated with reduced cellular cAMP in a patient, such as inflammatory diseases of the respiratory tract including, for example, asthma, chronic obstructive pulmonary disease (COPD), acute respiratory distress syndrome, bronchitis, chronic bronchitis, silicosis, pulmonary fibrosis, lung allograft rejection, allergic rhinitis and chronic sinusitis as well as other conditions in which an increase in cyclic AMP or a decrease in PDE levels is beneficial.

12 Claims, 14 Drawing Sheets

OTHER PUBLICATIONS

Ishii, Y et al., "Induction of Matrix Metalloproteinase Gene Transcription by Nitric Oxide and Mechanisms of MMP-1 Gene Induction in Human Melanoma Cell Lines." Int J Cancer 103:161-168, 2003.

Müller, T et al., "Subtypes of the type 4 cAMP phosphodiesterases: structure, regulation and selective inhibition." TiPS 17:294-298, 1996.

Weintraub, HM, "Antisense RNA and DNA." Scientific American 262(1):40-46, 1990.

Némoz, G et al., "Identification of cyclic AMP-phosphodiesterase variants from the PDE4D gene expressed in human peripheral mononuclear cells." FEBS Letters 384:97-102, 1996.

Wang, P et al., "Cloning, Characterization, and Tissue Distribution of Mouse Phosphodiesterase 7A1." Biochemical and Biophysical Research Communications 276:1271-1277, 2000.

Clayton, RA et al., "The effect of selective phosphodiesterase inhibitors, alone and in combination, on a murine model of allergic asthma." Respiratory Research 5:4(1-9), 2004.

McCluskie, K et al., "Phosphodiesterase type 4 inhibitors cause pro-inflammatory effects in vivo." American Society for Pharmacology and Experimental Therapeutics JPET #105080, 2006.

Smith, SJ et al, "Discovery of BRL 50481 [3-(N,N-dimethylsulfonamido)-4-methyl-nitrobenzene], a Selective Inhibitor of Phosphodiesterase 7: In Vitro Studies in Human Monocytes, Lung Macrophages, and CD8+ T-Lymphocytes." Molecular Pharmacology 66:1679-1689, 2004.

Robichaud, A et al., "Deletion of phosphodiesterase 4D in mice shortens alpha2-adrenoceptor-mediated anesthesia, a behavioral correlate of emesis." J Clin Invest 110:1045-1052, 2002.

Robichaud, A et al., "Assessing the emetic potential of PDE4 inhibitors in rats." British Journal of Pharmacology 135:113-118, 2002.

Calverley, PMA et al, "Effect of 1-Year Treatment with Roflumilast in Severe Chronic Obstructive Pulmonary Disease." Am J Respir Crit Care Med 176:154-161, 2007.

Dietsch, GN et al., "Characterization of the Inflammatory Response to a Highly Selective PDE4 Inhibitor in the Rat and the Identification of Biomarkers that Correlate with Toxicity." Toxicologic Pathology 34:39-51, 2006.

Epstein, Methods: A Companion to Methods in Enzymology, Article No. ME970562, 14:21-33 (1998). "Antisense Inhibition of Phosphodiesterase Expression."

Li et al., Science, 283:848-851 (1999). "CD3- and CD28-Dependent induction of PDE7 Required for T-Cell Activation."

MacKenzie et al., Proc National Academic Science, USA, 95:3549-3554 (1998). "Stimulation of p70S6 Kinase Via a Growth Hormone-Controlled Phosphatidylinositol 3-Kinase Pathway Leads to the Activation of a PDE4A Cyclic AMP-Specific Phosphodiesterase in 3T3-F442A Preadipocytes."

Soderling et al., Current Opinion in Cell Biology, 12:174-179 (2000). "Regulation of cAMP and cGMP Signaling: New Phosphodiesterases and New Functions."

* cited by examiner

A

B

C

A

B

C

OLIGONUCLEOTIDE COMPOSITIONS AND METHODS FOR TREATING DISEASE INCLUDING INFLAMMATORY CONDITIONS

CROSS-REFERENCE TO RELATED APPLICATIONS

The present application is a divisional of U.S. Ser. No. 10/953,512 filed on Sep. 29, 2004, which issued on Aug. 25, 2009 as U.S. Pat. No. 7,579,455, which claims the benefit under 35 U.S.C §119(e) of U.S. provisional Application No. 60/507,016, filed Sep. 29, 2003, the disclosure of which is incorporated herein by reference in its entirety.

FIELD OF THE INVENTION

The invention relates to methods, reagents and compositions of use for antisense oligonucleotide-based therapy. In particular, the invention relates the application of antisense oligonucleotide-based therapy in the treatment of disease associated with reduced cAMP in a patient including, for example, PDE-related disease such as inflammatory conditions. The invention also relates to gene therapy methods and methods for identifying novel antisense-based strategy wherein cyclic AMP phosphodiesterases are involved.

BACKGROUND OF THE INVENTION

The alveolar and airway epithelium is recognized as a dynamic barrier that plays an important role in regulating the inflammatory and metabolic responses to oxidative stress, sepsis, endotoxemia, and other critical illnesses in the lung. The respiratory epithelium, in particular, is a primary target of an inflammatory/infectious condition at the epithelial-blood interface, and is itself capable of amplifying an inflammatory signal by recruiting inflammatory cells and producing inflammatory mediators.

Chronic Obstructive Pulmonary Disease (COPD) is one example of an inflammatory airway and alveolar disease where persistent upregulation of inflammation is thought to play a role. Inflammation in COPD is characterized by increased infiltration of neutrophils, CD8 positive lymphocytes, and macrophages into the airways. Neutrophils and macrophages play an important role in the pathogenesis of airway inflammation in COPD because of their ability to release a number of mediators including elastase, metalloproteases, and oxygen radicals that promote tissue inflammation and damage. It has been suggested that inflammatory cell accumulation in the airways of patients with COPD is driven by increased release of pro-inflammatory cytokines and of chemokines that attract the inflammatory cells into the airways, activate them and maintain their presence. The cells that are present also release enzymes (like metalloproteases) and oxygen radicals which have a negative effect on tissue and perpetuate the disease. A vast array of pro-inflammatory cytokines and chemokines have been shown to be increased within the lungs of patients with COPD. Among them, an important role is played by tumor necrosis factor alpha (TNF-alpha), granulocyte-macrophage colony stimulating factor (GM-CSF) and interleukin 8 (IL-8), which are increased in the airways of patients with COPD.

Other examples of respiratory diseases where inflammation seems to play a role include: asthma, eosinophilic cough, bronchitis, acute and chronic rejection of lung allograft, sarcoidosis, pulmonary fibrosis, rhinitis and sinusitis. Asthma is defined by airway inflammation, reversible obstruction and airway hyperresponsiveness. In this disease the inflammatory cells that are involved are predominantly eosinophils, T lymphocytes and mast cells, although neutrophils and macrophages may also be important. A vast array of cytokines and chemokines have been shown to be increased in the airways and play a role in the pathophysiology of this disease by promoting inflammation, obstruction and hyperresponsiveness.

Eosinophilic cough is characterized by chronic cough and the presence of inflammatory cells, mostly eosinophils, within the airways of patients in the absence of airway obstruction or hyperresponsiveness. Several cytokines and chemokines are increased in this disease, although they are mostly eosinophil directed. Eosinophils are recruited and activated within the airways and potentially release enzymes and oxygen radicals that play a role in the perpetuation of inflammation and cough.

Acute bronchitis is an acute disease that occurs during an infection or irritating event for example by pollution, dust, gas or chemicals, of the lower airways. Chronic bronchitis is defined by the presence of cough and phlegm production on most days for at least 3 months of the year, for 2 years. One can also find during acute or chronic bronchitis within the airways inflammatory cells, mostly neutrophils, with a broad array of chemokines and cytokines. These mediators are thought to play a role in the inflammation, symptoms and mucus production that occur during these diseases.

Lung transplantation is performed in patients with end stage lung disease. Acute and more importantly chronic allograft rejection occur when the inflammatory cells of our body, lymphocytes, do not recognize the donor organ as "self". Inflammatory cells are recruited by chemokines and cytokines and release a vast array of enzymes that lead to tissue destruction and in the case of chronic rejection a disease called bronchiolitis obliterans.

Sarcoidosis is a disease of unknown cause where chronic non-caseating granulomas occur within tissue. The lung is the organ most commonly affected. Lung bronchoalveolar lavage shows an increase in mostly lymphocytes, macrophages and sometimes neutrophils and eosinophils. These cells are also recruited and activated by cytokines and chemokines and are thought to be involved in the pathogenesis of the disease.

Pulmonary fibrosis is a disease of lung tissue characterized by progressive and chronic fibrosis (scarring) which will lead to chronic respiratory insufficiency. Different types and causes of pulmonary fibrosis exist but all are characterized by inflammatory cell influx and persistence, activation and proliferation of fibroblasts with collagen deposition in lung tissue. These events seem related to the release of cytokines and chemokines within lung tissue.

Acute rhinitis is an acute disease that occurs during an infection or irritating event, for example, by pollution, dust, gas or chemicals, of the nose or upper airways. Chronic rhinitis is defined by the presence of a constant chronic runny nose, nasal congestion, sneezing and pruritis. One can also find within the upper airways during acute or chronic rhinitis inflammatory cells with a broad array of chemokines and cytokines. These mediators are thought to play a role in the inflammation, symptoms and mucus production that occur during these diseases.

Acute sinusitis is an acute, usually infectious disease of the sinuses characterized by nasal congestion, runny, purulent phlegm, headache or sinus pain, with or without fever. Chronic sinusitis is defined by the persistence for more than 6 months of the symptoms of acute sinusitis. One can also find during acute or chronic sinusitis within the upper airways and sinuses inflammatory cells with a broad array of chemokines and cytokines. These mediators are thought to play a role in the inflammation, symptoms and phlegm production that occur during these diseases.

As described above, these inflammatory respiratory diseases are all characterized by the presence of mediators that recruit and activate different inflammatory cells which release enzymes or oxygen radicals causing symptoms, the persistence of inflammation and when chronic, destruction or disruption of normal tissue.

A logical therapeutic approach would be to downregulate cytokine and chemokine production and the inflammatory cell response. This has been performed in all the diseases described above by employing either topical or systemic corticosteroids with different levels of success. Corticosteroids are immune suppressive and have effects not only on inflammatory cells but also on other cells of the body that lead to toxicity when administered chronically.

Despite the availability of medications for COPD, asthma and other inflammatory respiratory diseases, the prevalence and morbidity of these diseases has remained stable or increased. It is obvious that there is an unmet medical need for the therapy of inflammatory respiratory diseases, and innovative therapeutic agents are urgently required. Antisense oligonucleotide-based therapy offers a new alternative approach to selectively decrease the expression of specific genes without the undesirable toxic effects of traditional therapeutic strategies. Antisense therapies are being investigated for the treatment of several diseases. It has been previously shown that antisense oligonucleotides directed against receptors for inflammatory mediators can be administered to the lungs and down-regulate their targets as described in WO9966037.

A therapeutic approach that would decrease pro-inflammatory cytokine and chemokine release by a vast array of cells while having a reduced effect on the release of anti-inflammatory mediators or enzymes may have an advantage over current therapies for inflammatory respiratory diseases or any other systemic inflammatory disease.

The cyclic nucleotides cAMP and cGMP are ubiquitous second messengers participating in signaling transduction pathways and mechanisms. Mammalian cells have evolved a complex and highly conserved complement of enzymes that regulate the generation and inactivation of cyclic nucleotides through multiple and complex feedforward and feedback mechanisms. Both cAMP and cGMP are formed from their respective triphosphates (ATP and GTP) by the catalytic activity of adenylyl (adenylate) or guanylyl (guanylate) cyclase, respectively as described in Essayan D. M. *Cyclic nucleotide phosphodiesterase (PDE) inhibitors and immunomodulation*. Biochem. Pharmacol., 1999, 57, 965-973. Inactivation of cAMP/cGMP is achieved by hydrolytic cleavage of the 3'-phosphodiester bond catalyzed by the cyclic-nucleotide-dependent phosphodiesterases (PDEs), resulting in the formation of the corresponding, inactive 5'-monophosphate as described in Essayan, 1999 and Perry M. J. and Higgs G. A. *Chemotherapeutic potential of phosphodiesterase inhibitors*. 1998, Curr Opin Chem Biol. 4:472-81.

It has been shown that the inflammatory response and its progression is exquisitely sensitive to modulations in the steady-state levels of cyclic nucleotides, where target cells for their effects extend beyond immune cells to include accessory cells, such as airway smooth muscle, epithelial and endothelial cells, and neurons as described in Perry and Higgs, 1998; Essayan, 1999. In this respect, the emerging concept that modulation of intracellular cyclic nucleotides plays a major role in regulating the inflammatory milieu has recently evolved into targeting and improving inflammatory/autoimmune responses. The cyclic nucleotide PDEs are a large, growing multigene family, comprising at least 11 families of PDE enzymes. The profile of selective and nonselective PDE inhibitors in vitro and in vivo, therefore, suggests a potential therapeutic utility as antidepressants, antiproliferative, immunomodulatory, tocolytics, inotropes/chronotropes, and cytoprotective agents.

Intracellular cAMP seems to have a fundamental role, not only in smooth muscle relaxation, activation and proliferation but also in the modulation of the release of mediators by inflammatory cells. Decreased cAMP levels can lead to increased production of inflammatory mediators such as TNF-alpha, GM-CSF, and IL-8 in airway epithelial cells.

Insight into the molecular mechanisms of the regulatory role of cytokines in cellular homeostasis as well as inflammatory/autoimmune/infectious diseases has begun to provide new approaches to design therapeutic strategies for pharmacological interventions. One such novel approach is the chemotherapeutic potential of PDE enzyme blockade, which revealed a phenomenal diversity and complexity scheme for promising therapeutics across a broad spectrum of disease states. One mechanistic understanding of PDE inhibition is centered on the immunomodulatory properties of cyclic nucleotides (cAMP/cGMP), thereby paving a channel through which anti-inflammatory, therapeutic applications could be clearly demonstrated.

The inflammatory response and its progression is exquisitely sensitive to modulations in the steady-state levels of cyclic nucleotides, where target cells for their effects extend beyond immune cells to include structural cells, such as epithelial, smooth muscle and endothelial cells, and neurons (Perry and Higgs, 1998; Essayan, 1999). Modulation of intracellular cyclic nucleotides plays a major role in regulating the inflammatory response. The cyclic nucleotide PDEs are a large, growing multigene family, comprising at least 11 families of PDE isoenzymes. PDEs differ in their tissue and cellular distribution as well as in their molecular and physicochemical characteristics including nucleotides and protein sequences, substrate specificity, inhibitor sensitivity, and cofactor requirements. Within different families, tissue specific isoforms are generated from the same gene by alternative mRNA splicing and differential promoter usage.

The cAMP-specific PDE4 enzyme family is one of the most extensively studied PDEs. Enzymes within this family are found in most pro-inflammatory and immune cells, where they play a key role in the regulation of cAMP metabolism. PDE4 enzymes are expressed in macrophages, neutrophils, cytotoxic CD8+ T cells, bronchial epithelial cells, and airway smooth muscle cells. Moreover, PDE4 inhibitors modulate inflammation in animal models of respiratory diseases, suggesting that PDE4 may represent a suitable target in a therapeutic based strategy for intervention with small molecule inhibitors. Anti-PDE4 drugs inhibit the hydrolysis of intracellular cAMP, which in turn provides bronchodilation and suppression of the inflammatory response. Selective PDE4 inhibitors such as cilomilast and roflumilast are active in animal models of neutrophil inflammation (Bundschuch D S et al. J. Pharmacol. Exp. Ther. 2001, 297: 280-290). Although the use of PDE4 inhibitors for the treatment of airway inflammation is under intensive clinical investigations, several inhibitors have been dropped because of their toxicity, dose-limiting side effects, of which nausea and vomiting are the most common physiological manifestations. Consequently, improving the therapeutic ratio of PDE4 inhibitors raised a major challenge that is still an important field of investigation.

Considering the distribution of enzymes in target tissues, with high activity of PDE3 and PDE4 in airway smooth muscle and inflammatory cells, selective inhibitors of these enzymes may add to the therapy of chronic airflow obstruction. Generally small molecule inhibitors have been focused on one or several PDE without assessing the potential detrimental effects of inhibiting all the isoenzymes of a PDE. For example it has been suggested that most of the toxicity attributed to the PDE4 antagonists will occur through inhibition of the PDE4 isotype D. In addition, as shown herein, inhibition of certain isoenzymes of PDEs does not decrease all pro-inflammatory mediators however, a combination of isotype specific oligonucleotides can lead to an effect that is much broader when the right combination of antisense oligonucleotides is employed.

The PDE3 family contains two different genes, PDE3A and PDE3B, which are cGMP-inhibited and display a high affinity towards cAMP. Each PDE3 gene codes for at least two splice isoforms. The PDE3A has been identified in smooth muscle, platelets and cardiac tissues. The PDE3B is most abundant in adipocytes and liver cells. However, initial data from clinical trials with selective PDE3 inhibitors or a combination with PDE4 inhibitors have been somewhat disappointing and have tempered the expectations considerably since these drugs had limited efficacy and their use was clinically limited through side effects.

PDE7 was first isolated from a human glioblastoma. PDE7A codes for a cAMP-specific PDE that is insensitive to cGMP and inhibitors of PDE3 and PDE4 and has an amino acid sequence distinct from other cAMP PDEs. In humans two genes (PDE7A and PDE7B) have been characterized. The PDE7A gene codes for three isoenzymes (PDE7A1, PDE7A2, and PDE7A3) derived from the same gene by alternative mRNA splicing. In humans, PDE7A2 mRNA is expressed abundantly in skeletal muscle, heart, and kidney, whereas the testis, lung, and immune system (thymus, spleen, lymph node, blood leukocytes) are rich sources of PDE7A1. In addition, activated, but not naïve, human T lymphocytes express the splice variant PDE7A3. In contrast, PDE7B exists as a single isoenzyme in humans, it shares ~70% sequence similarity to PDE7A, but distinct kinetic properties. PDE7B is expressed predominantly in the brain and in a number of other tissues including liver, heart, thyroid glands, and skeletal muscle. Stimulation of human naïve T cells with anti-CD3 and anti-CD28 antibodies has been shown to promote IL-2 production and clonal amplification. These effects were attributed to PDE7A and down regulation of this enzyme prevents lymphocyte proliferation (Li L et al., Science, 1999, 283, 848-851).

The PDE4 family contains 4 different genes (PDE4 A-D). Due to alternative splicing of the genes, multiple splice variants are reported and classified into two main groups, the long and the short forms. PDE4A, B and D gene products are found in most immune and inflammatory cells. These are present either constitutively or after activation as described in Burnouf C. and Pruniaux M. P. Current Pharmaceutical Design 2002; 8:1255-1296. Inhibition of all or certain isotypes of PDE4 is associated with downregulation of several inflammatory mediators; however, an increase in certain pro-inflammatory cytokines (e.g. IL-6) has been described (Giembycz M. A. Expert Opin Invest Drugs 2001, 10:1361-1379).

It would therefore be desirable to inhibit all three PDE enzymes; however this approach may be plagued by the toxicity that has been described with administration of inhibitors of each of these enzymes. The topical application of antisense oligonucleotides could circumvent the systemic toxicity of enzyme inhibition but there appear to be too many isoenzymes of these PDE for this approach to be practical. Inhibition of one or several isotypes of PDE enzymes may not be as effective as full PDE inhibition since other isotypes would be present to have their pro-inflammatory effects.

It would therefore appear desirable to seek a way to down-regulate pro-inflammatory mediators and their cells while affecting less anti-inflammatory mediators or inhibitory enzymes for the therapy of inflammatory respiratory diseases. The therapeutic application of a combination of antisense oligonucleotides directed against selected isotypes of PDE enzymes is therefore herein proposed as a therapy for inflammatory respiratory diseases or any disease where increased cyclic AMP plays a role.

SUMMARY OF THE INVENTION

The present invention provides antisense oligonucleotide compounds that are effective at down-regulating PDE isotype genes that they are directed against as well as selected antisense oligonucleotide compounds that are effective at down-regulating not only the PDE isotype genes they are directed against but also other related genes including other PDE isotype genes and inflammatory genes. The present invention also provides a composition comprising a combination of at least two antisense oligonucleotide compounds each directed against a different PDE target gene and each being effective to downregulate or inhibit a PDE target gene, each oligonucleotide compound being present in the combination at a concentration at which it exhibits less than 20% inhibition of its target gene, the combination of the oligonucleotide compounds exhibiting more than 20% inhibition and at least doubling the inhibition of at least one of the target genes. The present invention further provides pharmaceutical compositions comprising a pharmaceutically acceptable carrier and a combination of at least two antisense oligonucleotides as described above.

The combinations of the present invention appear to exert an inhibitory action by an approach that has been termed multiple gene knock down. Multiple gene knock down encompasses situations in which:

1) an antisense oligonucleotide downregulates not only the gene that it is directed against but also downregulates other related genes; and
2) a combination of at least 2 antisense oligonucleotides, each present at a concentration at which the antisense oligonucleotide is practically ineffective to downregulate the gene it is directed against on its own, the combination leading to significant downregulation of both genes that the antisense oligonucleotides are directed against and optionally other related genes.

The present invention uses the above approach to provide methods, compositions and kits for treating and/or preventing disease associated with reduced cAMP in a patient, including PDE-related disease and inflammatory disease including respiratory diseases and more particularly COPD and asthma.

The present invention provides a composition comprising at least 2 antisense oligonucleotide compounds, each antisense oligonucleotide compound being capable of downregulating a different gene, each antisense oligonucleotide compound being present at a concentration at which the antisense oligonucleotide compound is practically ineffective on its own to downregulate the gene it is directed against, the combination of the at least 2 antisense oligonucleotide compounds leading to a significant downregulation of each of the genes that the antisense oligonucleotide compounds are directed against and optionally other related genes. The present invention also provides for the use of the composition in the treatment and/or prevention of inflammatory respiratory diseases.

The present invention provides a composition comprising at least 2 antisense oligonucleotides capable of downregulating different PDE isozyme genes, each oligonucleotide being present at a concentration at which the oligonucleotide is practically ineffective on its own to downregulate the PDE gene it is directed against, the combination of the at least 2 oligonucleotides leading to a significant downregulation of both genes that the oligonucleotides are directed against and optionally other related genes. The present invention also provides for the use of the composition in the treatment and/or prevention of inflammatory respiratory diseases.

The invention also provides methods, reagents and compositions for reducing the expression and consequently the activity of cell cyclic-AMP phosphodiesterases and thereby maintaining the correct balance of intracellular c-AMP and cytokine/chemokine production.

The invention further provides methods and tools for identifying/screening in vitro, in vivo and ex vivo, combinations of novel antisense oligonucleotide compounds, drugs and vaccines that are capable of interfering with PDE expression and elevating the intracellular c-AMP level.

The present invention also provides gene-based therapy and transfection methods in which one or more antisense oligonucleotide compounds are used for cell transfection or delivered to humans and animals for interfering with PDE isotype gene expression.

The present invention further provides antisense oligonucleotides effective against PDE3 isotypes, such as PDE3A and PDE3B; PDE4 isotypes such as PDE4A, PDE4B and PDE4D and PDE7 isotypes such as PDE7A, among other PDEs.

The present invention further provides an antisense oligonucleotide effective in the compositions and methods of the present invention having a sequence selected from the group consisting of; SEQ. ID NO.: 1; SEQ. ID NO.: 2; SEQ. ID NO.: 3; SEQ. ID NO.: 4; SEQ. ID NO.: 5; SEQ. ID NO.: 6; SEQ. ID NO.: 7; SEQ. ID NO.: 8; SEQ. ID NO.: 9; SEQ. ID NO.: 10; SEQ. ID NO.: 11; SEQ. ID NO.: 12; SEQ. ID NO.: 13; SEQ. ID NO.: 14; SEQ. ID NO.: 15; SEQ. ID NO.: 16; SEQ. ID NO.: 17; SEQ. ID NO.: 18; SEQ. ID NO.: 19; SEQ. ID NO.: 20; SEQ. ID NO.: 21; SEQ. ID NO.: 22; SEQ. ID NO.: 23; SEQ. ID NO.: 27; SEQ. ID NO.: 28; SEQ. ID NO.: 33; SEQ. ID NO.: 34; SEQ. ID NO.: 35; SEQ. ID NO.: 36; SEQ. ID NO.: 24; SEQ. ID NO.: 25; SEQ. ID NO.: 26; SEQ. ID NO.: 29; SEQ. ID NO.: 30; SEQ. ID NO.: 31; SEQ. ID NO.: 32 (Table 1a-f).

Other objects and advantages of the present invention will be apparent upon reading the following non-restrictive description of several preferred embodiments made with reference to the accompanying drawings.

BRIEF DESCRIPTION OF THE DRAWINGS

The present invention will be better understood with reference to the following description and to the Figures in which.

A.

Figure 3A:
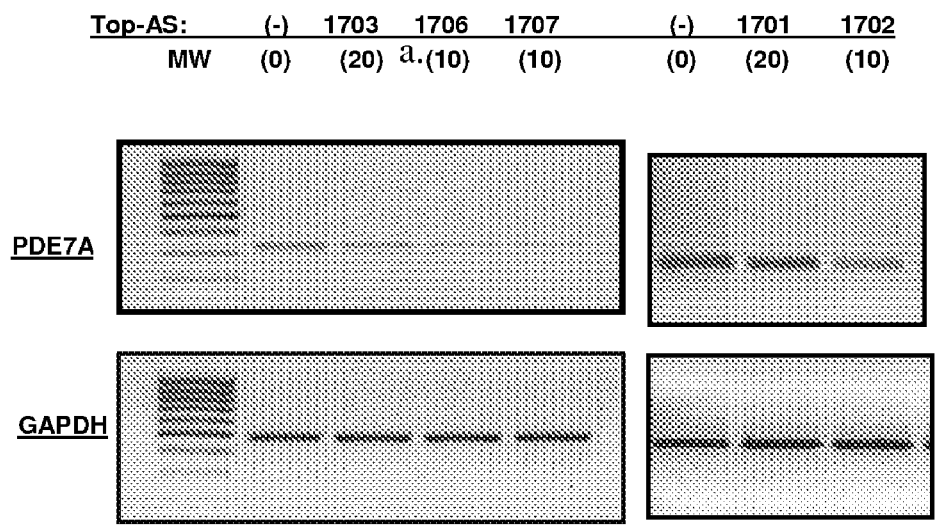
Figure 3B:
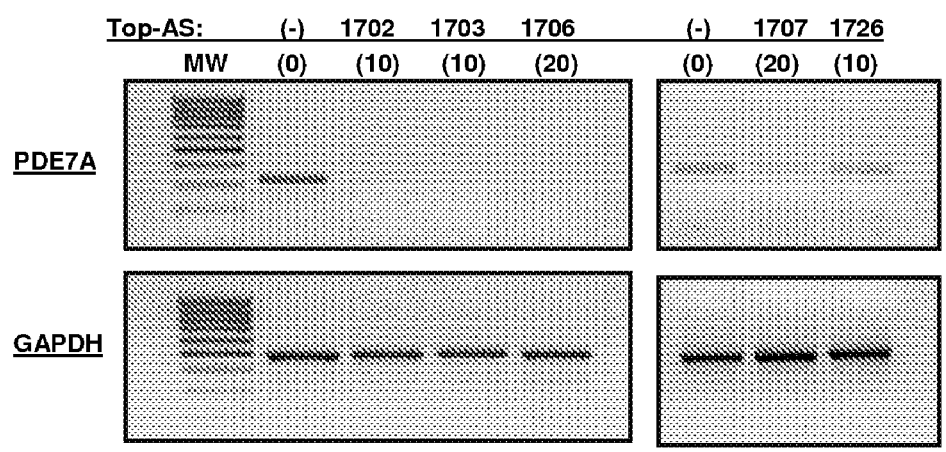
Figure 4A:
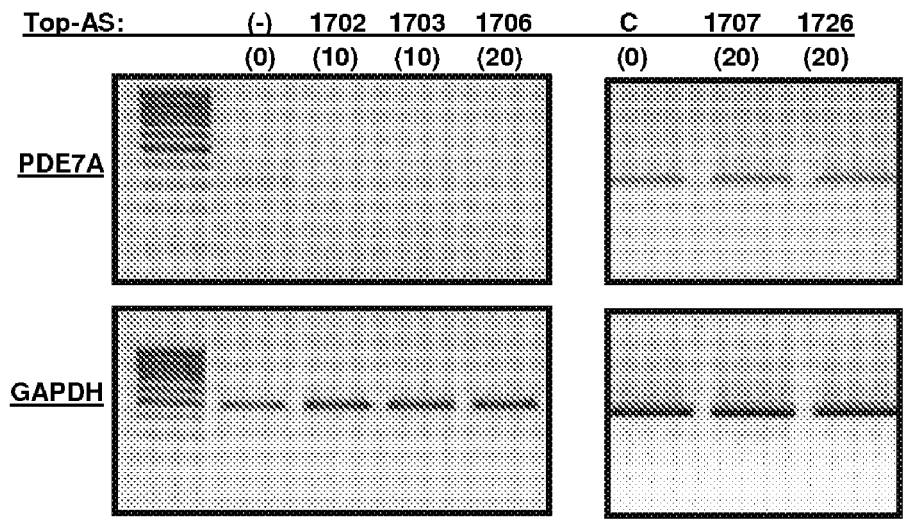
Figure 4B:
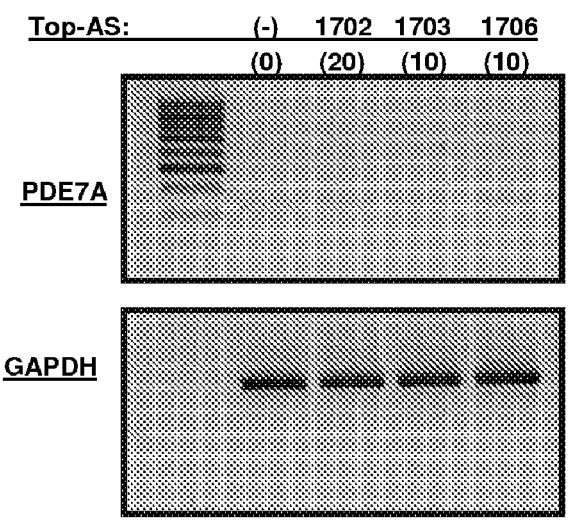
Figure 5A:
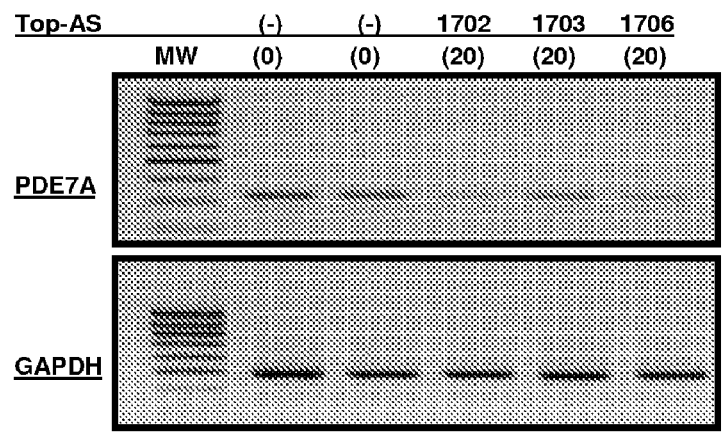
Figure 5B:
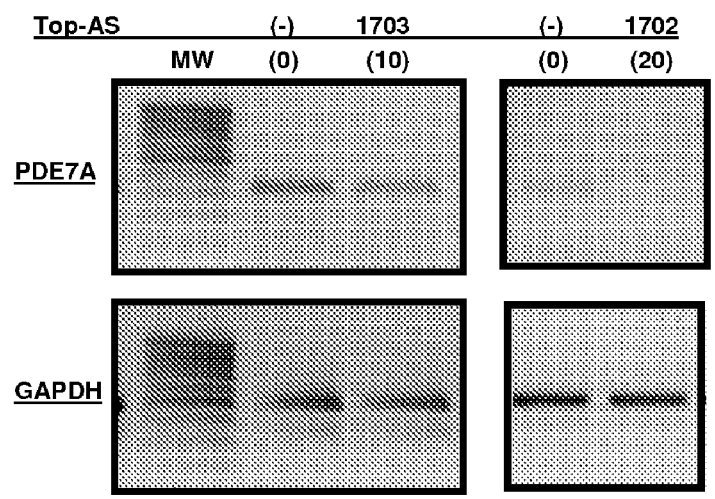
Figure 6A:
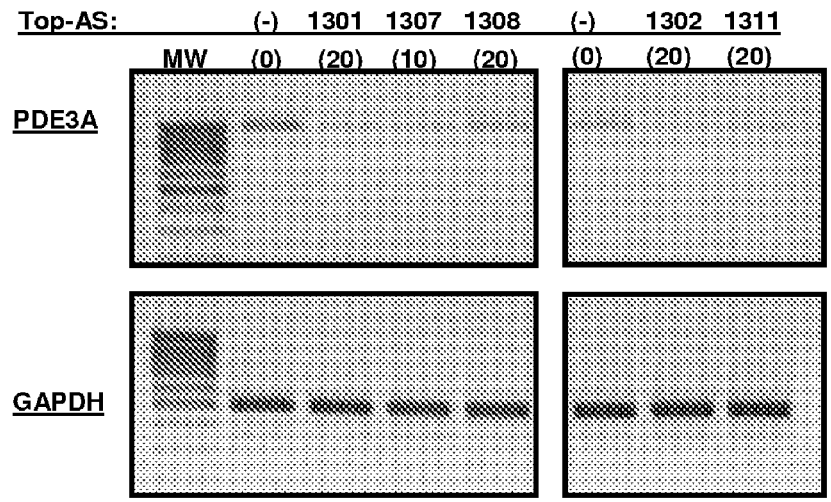
Figure 6B:
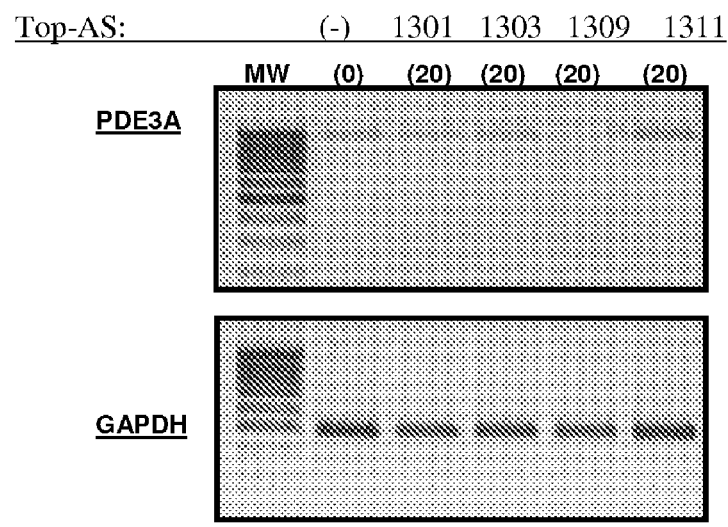
Figure 7:
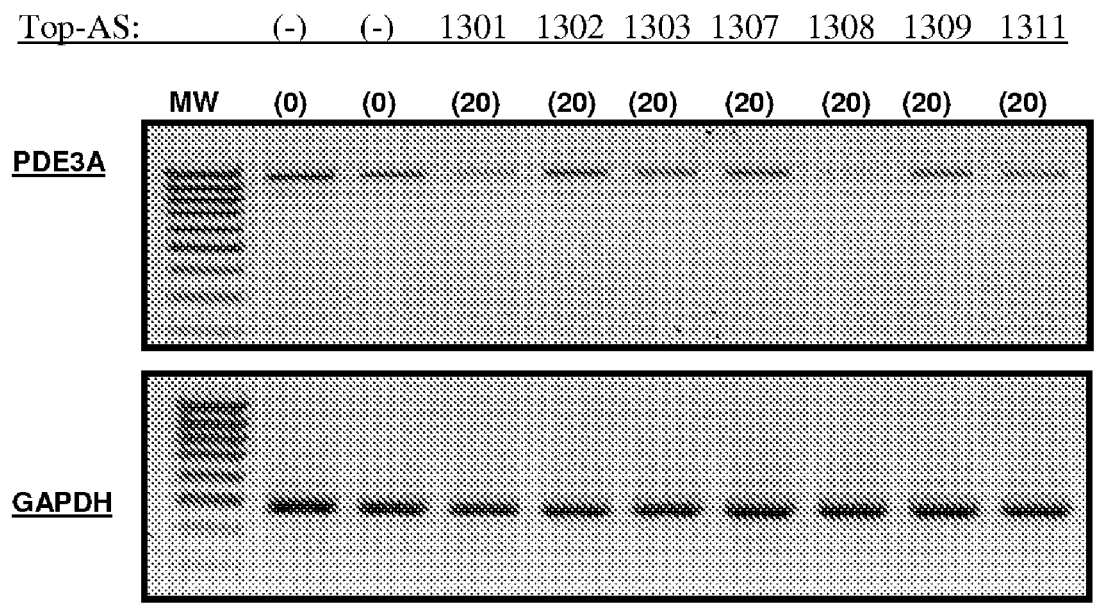
Figure 8:
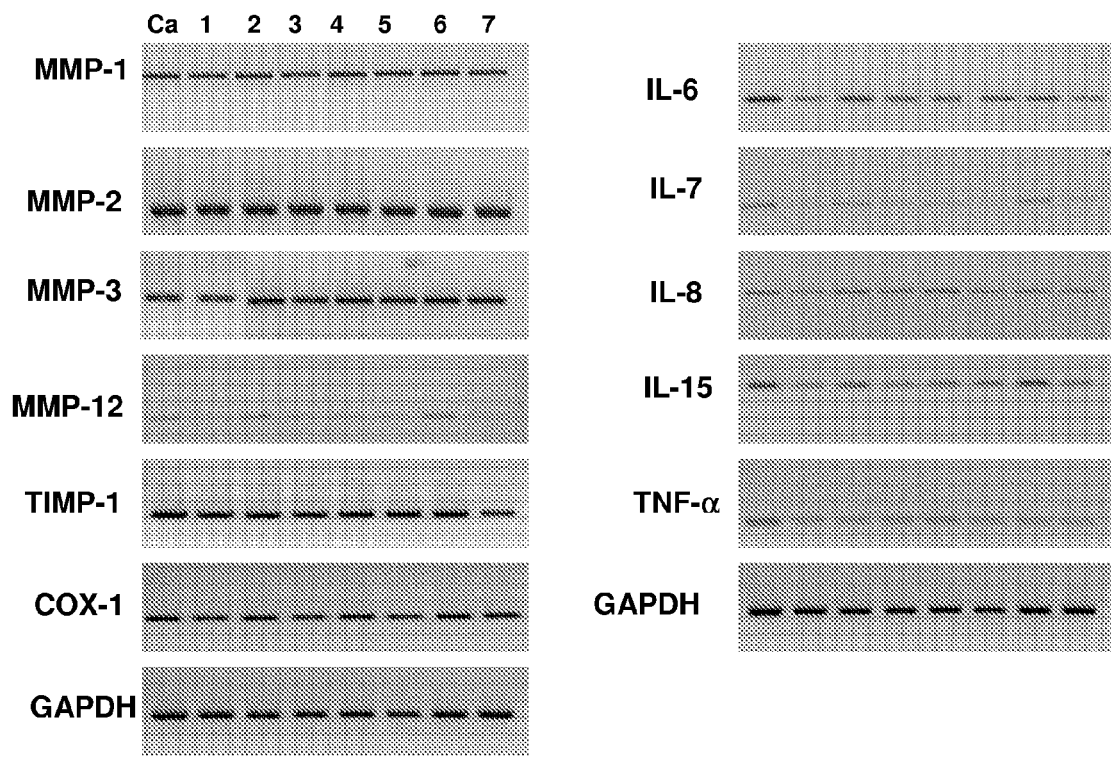
Figure 9:
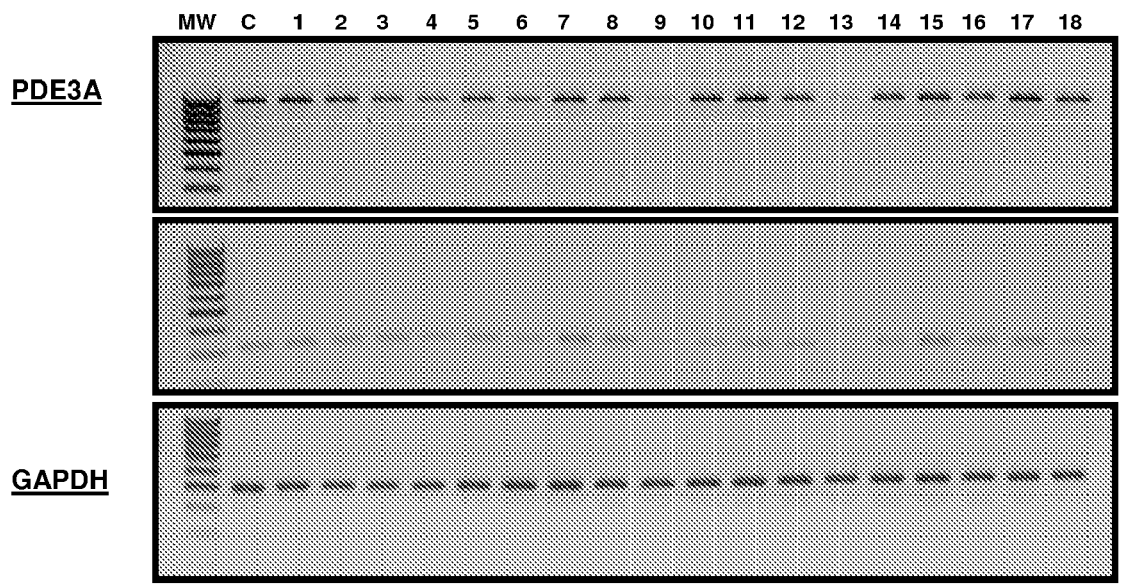
Figure 10:
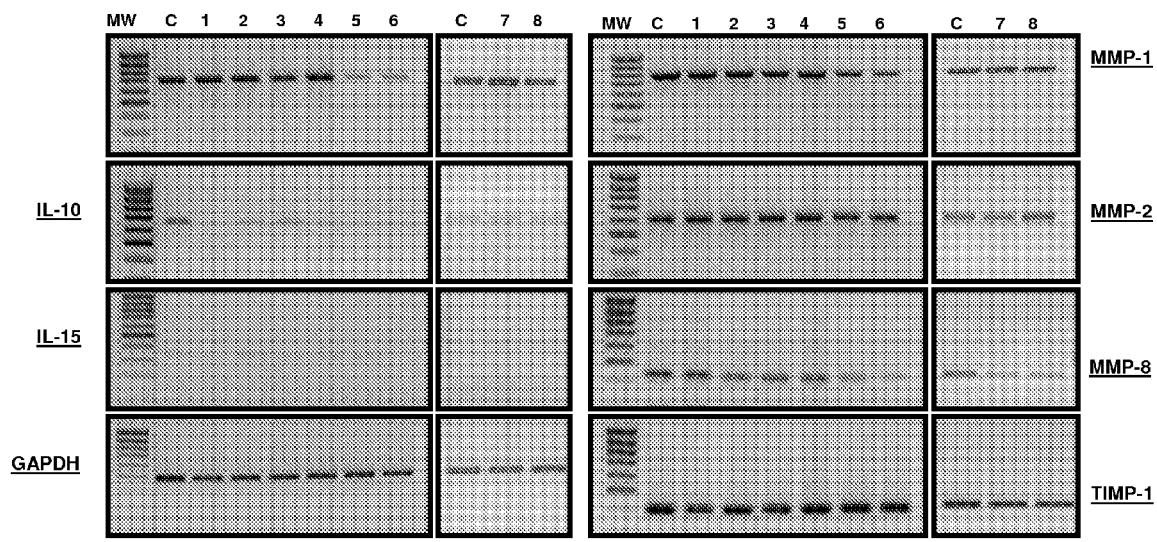
Figure 11:
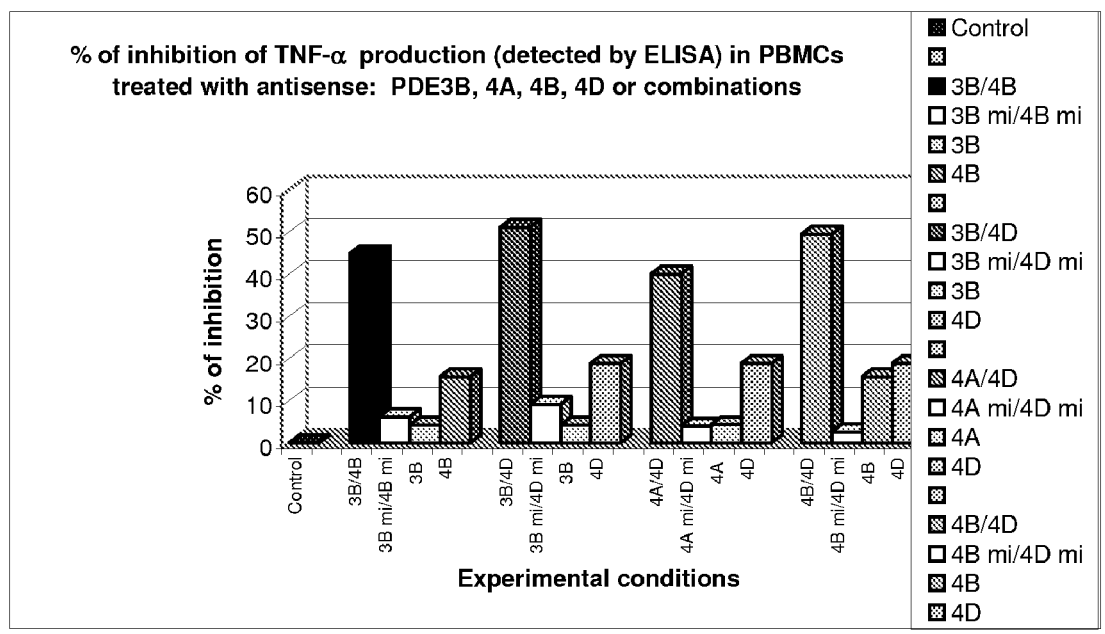
Figure 12:
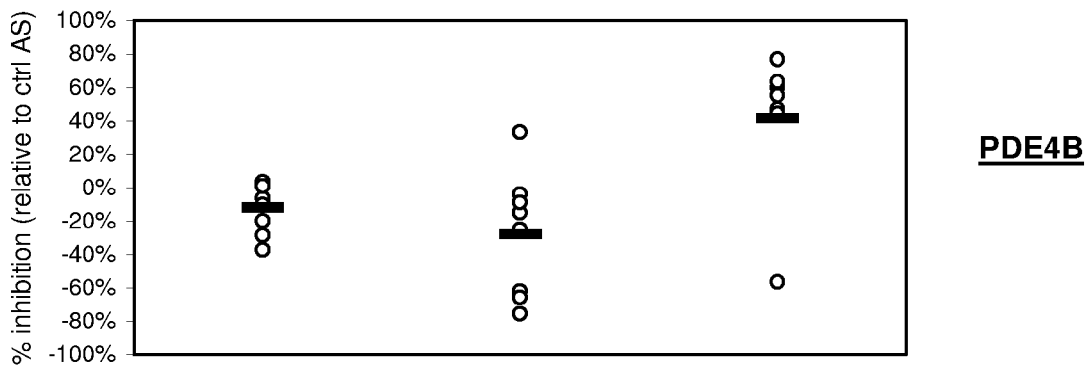
Figure 12:
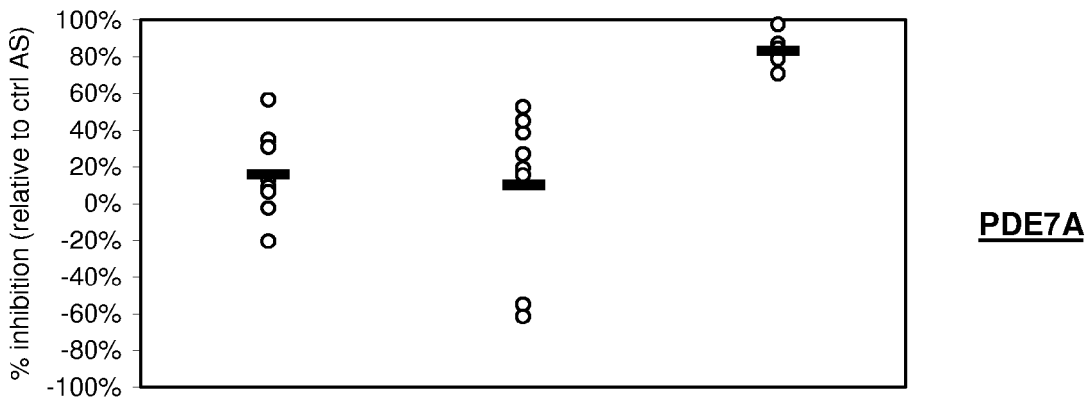
Figure 12:
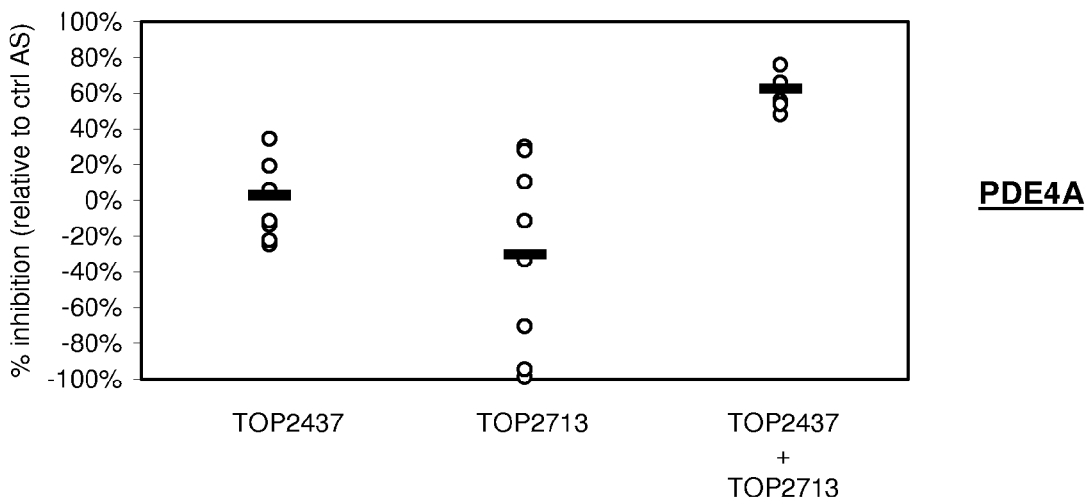
Figure 13:
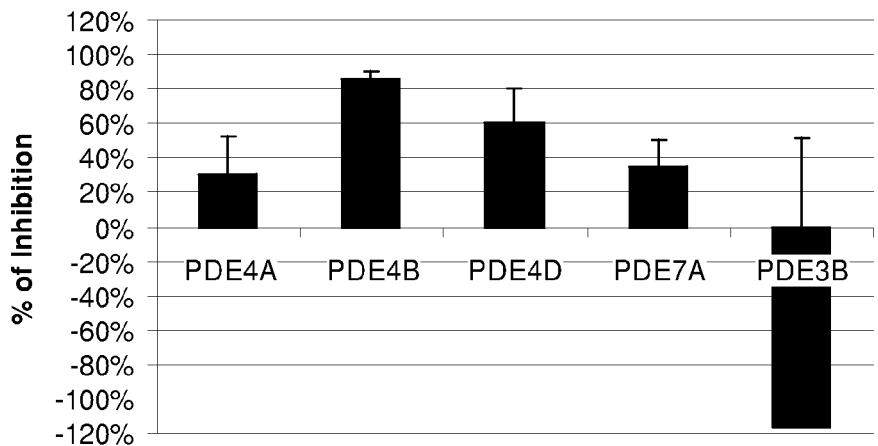
Figure 13:
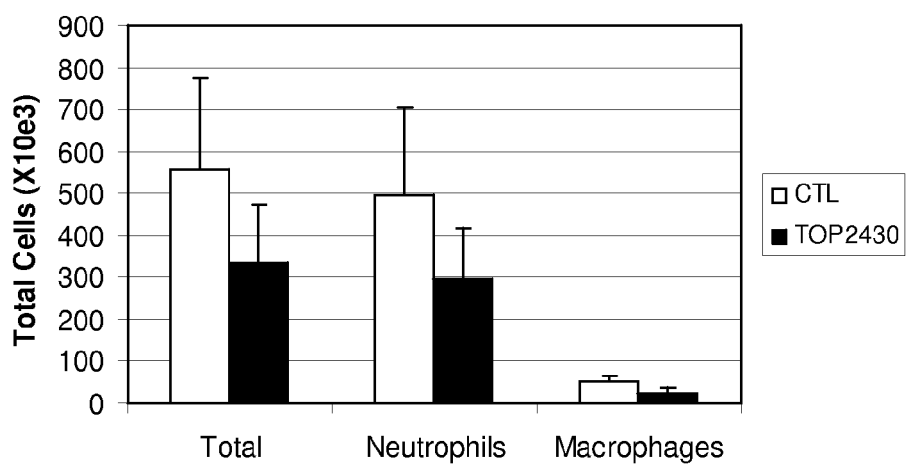
Figure 13:
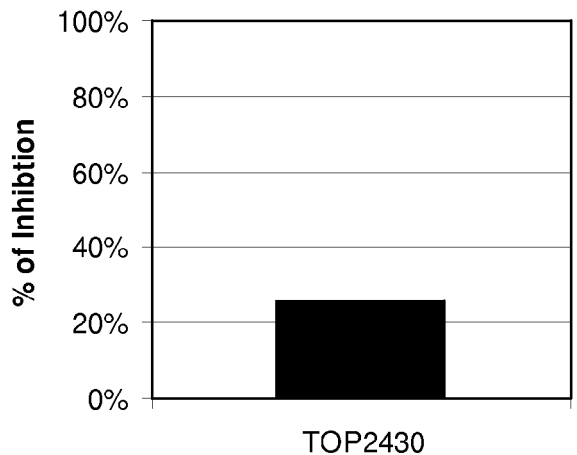
Figure 14:
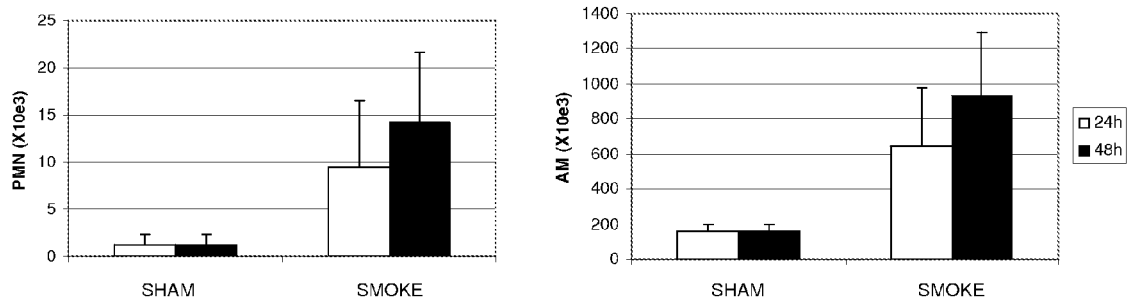
Figure 14:
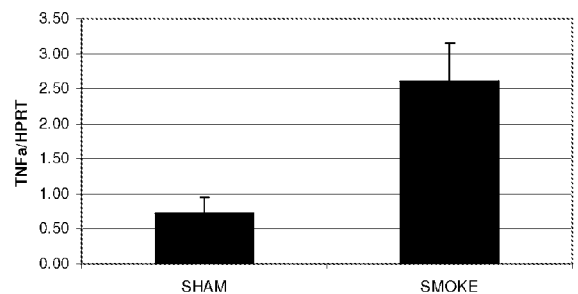
Figure 14:
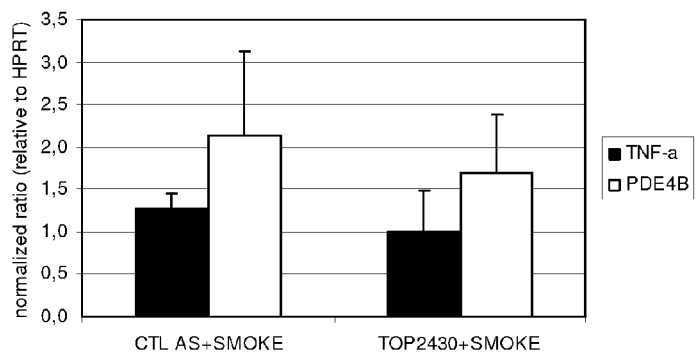

FIG. 3 illustrates 8 gels of semi-quantitative PCRs showing efficacy of some of the 1700 antisense series at decreasing PDE7A mRNA expression in Eol-1 and U937 cells. C=no antisense; Top-1701, Top-1702, Top-1703, Top-1706, Top-1707 and Top-1726=PDE7A-directed antisenses; 100 bp=DNA ladder; (0), (10) and (20)=antisense concentration in uM (micro-molar);

FIG. 4 illustrates 6 gels of semi-quantitative PCRs showing efficacy of some of the 1700 antisense series at decreasing PDE7A mRNA expression in Jurkat and Hut-78 cells. C=no antisense; Top-1702, Top-1703, Top-1706, Top-1707 and Top-1726=PDE7A-directed antisenses; 100 bp=DNA ladder; (0), (10) and (20)=antisense concentration in uM (micro-molar);

FIG. 5 illustrates 6 gels of semi-quantitative PCRs showing efficacy of some of the 1700 antisense series at decreasing PDE7A mRNA expression in BSMC and A549 cells. C1 and C2=no antisense; Top-1702, Top-1703, and Top-1706=PDE7A-directed antisenses; MW=100 bp DNA ladder; (0), and (20)=antisense concentration in uM (micro-molar);

FIG. 6 illustrates 6 gels of semi-quantitative PCRs showing efficacy of some of the 1300 antisense series at decreasing PDE3A mRNA expression in A549 and U937 cells. C=no antisense; Top-1301, Top-1302, Top-1303, Top-1307, Top-1308, Top-1309 and Top-1311=PDE3A-directed antisenses; 100 bp=DNA ladder; (0), (10) and (20)=antisense concentration in uM (micro-molar);

FIG. 7 illustrates a gel of semi-quantitative PCRs showing the efficacy of the 1300 antisense series at decreasing PDE3A mRNA expression in BSMC cells. C1 and C2=no antisense; Top-1301, Top-1302, Top-1303, Top-1307, Top-1308, Top-1309 and Top-1311=PDE3A-directed antisenses; 100 bp=DNA ladder; (0), and (20)=antisense concentration in uM (micro-molar);

FIG. 8 illustrates semi-quantitative PCRs showing the relative efficacy of the antisense oligonucleotides of the 1300 and the 1700 antisense series at decreasing MMP-1, MMP-2, MMP-3, MMP-12, TIMP-1, COX-1, IL-6, IL-7, IL-8, IL-15, TNF-alpha in BSMC cells. C=no antisense; Top-1301, Top-1303, Top-1308, and Top-1311=PDE3A-directed antisenses; Top-1702, Top-1703, and Top-1706=PDE7A-directed antisenses; MW=100 bp DNA ladder;

FIG. 9 illustrates a gel of semi-quantitative PCRs showing the efficacy and the concept of multiple gene knock down of PDE3A and PDE7A mRNA expression by combinations of oligos from the 1700 and 1300 series in U937 cells. C=no antisense; 1=Top-1301; 2=Top-1303; 3=Top-1307; 4=Top-1311; 5=Top-1702; 6=Top-1703; 7=Top-1706; 8=Top-1702 and 1301; 9=Top-1703 and Top-1301; 10=Top-1706 and Top-1301; 11=Top-1702 and Top-1303; 12=Top-1703 and Top-1303; 13=1706 and 1303; 14=Top-1702 and Top-1307; 15=Top-1703 and Top-1307; 16=Top-1706 and Top-1307; 17=Top-1703 and Top-1311; 18=Top-1706 and Top-1311; MW=100 bp DNA ladder. The combinations 9 and 13 are the ones that are effective at multiple gene knock down;

FIG. 10 illustrates semi-quantitative PCRs showing the relative efficacy and concept of multiple gene knock down of the 1300 and the 1700 antisense series at modulating the expression level of PDE4B, IL-10, IL-15, MMP-1, MMP-2, MMP-8, TIMP-1 in U937 cells. C=no antisense; Top-1301, Top-1303, Top-1307 and Top-1311=PDE3A-directed antisenses; Top-1703, and Top-1706=PDE7A-directed antisenses; MW=100 bp DNA ladder. 1=Top-1301; 2=Top-1303; 3=Top-1703; 4=Top-1706; 5=Top-1301 and Top-1703; 6=Top-1303 and 1706; 7=Top-1311 and Top-1703; 8=Top-1307 and Top-1703;

FIG. 11 shows the results of a functional assay for human PDE antisenses (AS) and their relative efficacy of multiple gene knock down at the level of TNF-alpha protein. The test assessed the effects of antisense oligonucleotides directed against different isotypes of PDEs on TNF-alpha production in human PBMC stimulated with PHA. PBMC were transfected with one AS, PDE3B AS: Top-1360 (SEQ. ID NO.: 19)=3B; PDE4B AS Top-1437 (SEQ. ID NO.: 28)=4B; PDE4D AS Top-1498 (SEQ. ID NO.: 36)=4D; PDE4A AS Top-1413 (SEQ. ID NO.: 23)=4A. PBMC were also transfected with combinations of two AS, 3B/4B=Top-1360 (SEQ. ID NO.: 19)+Top-1437 (SEQ. ID NO.: 28); 3B/4D=Top-1360 (SEQ. ID NO.: 19)+Top-1498 (SEQ. ID NO.: 36); 4A/4D=Top-1413 (SEQ. ID NO.: 23)+Top-1498 (SEQ. ID NO.: 36); 4B/4D=Top-1437 (SEQ. ID NO.: 28)+Top-1498 (SEQ. ID NO.: 36). Mismatch ASs (3Bmi, 4Ami, 4Bmi and 4Dmi) were also included in this study. PHA challenged but non transfected PBMC were considered as controls;

FIG. 12 shows the multiple target inhibition and synergistic effect of combined antisense treatment targeting both PDE4B and PDE7A. Mice (8 per group) were nasally instilled with 50 mg Top-2437 (targeting PDE4B), 50 mg Top-2713 (targeting PDE7A) or a combination of both antisenses (50 mg of each). Control mice received the same amount of control antisense oligonucleotide. Real-time PCR analysis was performed for (A) PDE4B, (B) PDE7A and (C) PDE4A expression, normalized to HPRT (reference gene) 16 h after instillation. Data represent % of inhibition for each mouse (relative to control antisense treated mice) of PDE4B expression, PDE7A expression and PDE4A expression. Bars indicate mean % of inhibition;

FIG. 13 shows the effect of specific inhibition by antisense oligonucleotides targeted at the PDE4B mRNA on LPS-induced lung inflammation and on PDE mRNA expression. A) Effect of the inhibition of PDE4B on the expression of other mRNA for PDEs. The expression levels of different PDE mRNAs in TOP2430 treated mice were assessed by real-time PCR 6 h after LPS exposure. % of inhibition were determined by comparing the expression levels obtained to the expression levels measured in mice that received the control antisense oligonucleotide. Values shown represent means +/− SD (n=8–9). B) Inhibition of the cellular influx in the lung of LPS-exposed mice pre-treated with TOP2430. Differential cell count of BAL cells was performed 6 h after LPS exposure. Values shown represent means +/− SD (n=8–9). C) Effect on TNF-alpha release in BAL. TNF-alpha release in TOP2430 treated mice was measured by ELISA and % of inhibition were determined by comparing TNF-alpha values obtained after TOP 2430 to the values obtained in mice treated with a control antisense oligonucleotide; and FIG. 14 shows the effect of specific inhibition by an antisense oligonucleotide targeting the mouse PDE4B mRNA on cigarette smoke-induced lung inflammation. A) Bronchoalveolar lavage cell counts 24 h and 48 h after cigarette smoke exposure. Values are mean +/− SD. PMN=neutrophils; AM=macrophages. B) TNF-alpha mRNA expression in lung tissue of mice exposed to cigarette smoke. The expression levels of TNF-alpha mRNA were assessed by real-time PCR on cDNA prepared from RNA isolated from whole lungs 48 h after cigarette smoke exposure (3 mice). Control mice were sham smoked (5 mice). Values are mean +/− SD of TNF-alpha expression relative to HPRT. C) TNF-alpha and PDE4B mRNA expression in mice pre-treated with TOP2430 (4 mice) or control antisense (5 mice) and exposed to cigarette smoke 3 h later. The expression levels of TNF-alpha and PDE4B mRNA were assessed by real-time PCR on cDNA prepared from RNA isolated from whole lungs 48 h after cigarette smoke exposure. Values are mean +/− SD of TNF-alpha or PDE4B expression relative to HPRT.

BRIEF DESCRIPTION OF THE TABLES

Table 1a identifies human PDE7A oligonucleotide antisenses in accordance with the present invention;

Table 1b identifies the human PDE3A oligonucleotide antisenses in accordance with the present invention;

Table 1c identifies the human PDE3B oligonucleotide antisenses in accordance with the present invention;

Table 1d identifies the human PDE4A oligonucleotide antisenses in accordance with the present invention;

Table 1e shows the human PDE4B oligonucleotide antisenses in accordance with the present invention;

Table 1f shows the human PDE4D oligonucleotide antisenses in accordance with the present invention;

Table 2a and 2b show human oligonucleotide primers used in standard PCR;

Table 2c shows human oligonucleotide primers used in real time PCR;

Table 2d shows mouse oligonucleotide primers used in real time PCR;

Table 3a and 3b show human PDE expression pattern in cell lines, primary cells and tissues;

Table 4a shows a summary of human PDE oligonucleotide antisenses primary screening in A549 cell line and in human PBMC;

Table 4b shows human PDE single antisenses with multiple gene knock down effects; and Table 5 shows mouse PDE oligonucleotide antisenses primary screening in vivo;

DETAILED DESCRIPTION OF THE INVENTION

The invention herein relates to antisense oligonucleotide-based compounds, therapeutic compositions and methods for the treatment of disease associated with reduced cellular cAMP and/or disease associated with elevated levels of at least one PDE. The invention is aimed at increasing the level of cAMP in cells, while decreasing the level of pro-inflammatory mediators as well as enzymes that are released by inflammatory cells.

To obtain these effects, the present invention utilizes, in one of its aspects, what is herein referred to as "multiple gene knock down". Multiple gene knock down refers to the inhibition or downregulation of multiple genes by either a single antisense oligonucleotide compound in accordance with the present invention which downregulates not only the isoenzyme gene that it is directed against but also a related gene(s), or by a combination of at least two antisense oligonucleotide compounds which each downregulate a different isoenzyme gene.

Diseases associated with reduced levels of cellular cAMP include diseases in which there is increased levels of at least one cAMP-specific PDE (i.e. a PDE-related disease).

The term "downregulate" is used herein to refer to at least partial inhibition of the expression of a gene. In accordance with the invention, an antisense oligonucleotide compound downregulates or inhibits a gene that it is directed against, i.e. a gene to which the antisense oligonucleotide compound exhibits sequence complementarity sufficient to cause inhibition.

The term "related genes" refers to other genes that may also play a role in the pathophysiology of disease associated with reduced cellular cAMP and/or increased levels of at least one PDE but to which the oligonucleotide antisense compound is not complementary, either wholly or partially. Such genes include, but are not limited to, genes that encode PDE enzymes or isotypes, mediators, for example, cytokines and chemokines and genes that encode enzymes. Examples of mediators include IL-6, IL-7, IL-8, IL-15 and TNF-alpha. Examples of appropriate enzymes include, but are not limited to, matrix metalloproteinases (MMPs), such as MMP-1, MMP-2, MMP-3, MMP-9 and MMP-12.

In accordance with the present invention, antisense oligonucleotide compounds are herein defined as oligonucleotides, naturally occurring or modified, preferably nuclease resistant, that exhibit a complementarity to DNA or mRNA coding for a particular target protein such that they are capable of interfering with the transcription or translation of the mRNA and/or induce RNase or RNase-like activity and thereby function to reduce expression of the target protein. Expression of the target protein is reduced when the oligonucleotide compound hybridizes to the target DNA or mRNA, thereby interfering/preventing its transcription/translation. The present oligonucleotide compounds, thus, must be sufficiently complementary to the nucleic acid to which it is directed in order to hybridize thereto. Thus, although in a most preferred embodiment, the oligonucleotide compounds are 100% complementary to the nucleic to which they are directed, 100% complementarity is not necessary for hybridization to occur between an oligonucleotide compound and the nucleic acid to which it is directed, as one of skill will appreciate.

The invention herein also relates to modifications to an antisense oligonucleotide(s) that do not significantly adversely effect their activity to reduce or inhibit expression of a target protein, but which may enhance this activity. The terms "nucleic acid" and "nucleic acid molecule" as used interchangeably herein, refer to a molecule comprised of nucleotides, i.e., ribonucleotides, deoxyribonucleotides, or both. The term includes monomers and polymers of ribonucleotides and deoxyribonucleotides, with the ribonucleotide and/or deoxyribonucleotides being connected together, in the case of the polymers, via 5' to 3' linkages. However, linkages may include any of the linkages known in the nucleic acid synthesis art including, for example, nucleic acids comprising 5' to 2' linkages. The nucleotides used in the nucleic acid molecule may be naturally occurring or may be synthetically produced analogues that are capable of forming base-pair relationships with naturally occurring base pairs. Examples of non-naturally occurring bases that are capable of forming base-pairing relationships include, but are not limited to, aza and deaza pyrimidine analogues, aza and deaza purine analogues, and other heterocyclic base analogues, wherein one or more of the carbon and nitrogen atoms of the purine and pyrimidine rings have been substituted by heteroatoms, e.g., oxygen, sulfur, selenium, phosphorus, and the like.

The present antisense oligonucleotide compounds may also be modified by insertion or deletion of 1 or more bases without significant adverse effect to their activity. In particular, the addition or deletion of bases at the terminal ends of the oligonucleotides that exhibit 100% complementation to the gene they are directed against can generally be made without significant loss of inhibitory activity. Such modifications may be made in order to increase activity or to provide enhanced stability of the oligonucleotide. In addition, substitution of 1 or more bases in the present antisense oligonucleotide compounds may also be made without adverse effect to activity, for example, substitution of purine with another purine (adenine, guanine) and pyrimidine with pyrimidine (cytosine, thymine, uracil).

Antisense oligonucleotide compounds in accordance with the present invention also include siRNAs (small interfering RNAs) and the RISCs (RNA-induced silencing complexes) containing them that result from the RNAi (RNA interference) approach. The RNA interference (RNAi) approach, which has been described recently, is considered as a new tool for the inhibition of target gene expression. As already known some years ago, RNAi is based on an ancient anti-viral defence mechanism in lower eukaryotes. It is induced by double-stranded RNA and its processing to 21-23 nt small interfering RNAs (siRNAs), which cause the degradation of homologous endogenous mRNA after hybridizing to the target mRNA in a single stranded fashion with the assistance of the RISC complex. The way RNAi works is still to be fully elucidated, but it already serves as a first-choice approach to generate loss-of-function phenotypes among a broad variety of eukaryotic species, such as nematodes, flies, plants, fungi and mammals.

Antisense oligonucleotide compounds in accordance with the present invention also include ribozymes and short nucleotide sequences, single or double stranded, RNA or DNA, which may incorporate chemical modifications as described above, capable of inhibiting gene transcription and/or translation in vitro and/or in vivo.

The compositions and methods of the present invention, in one aspect, while not to be bound by a particular mode of action, appear to act by a mechanism that has been termed "multiple gene knock down". Multiple gene knock down in the context of the present invention refers to:
1) an antisense oligonucleotide compound that downregulates not only the gene that it is directed against but also downregulates other related genes; and
2) a combination of at least 2 antisense oligonucleotide compounds each capable of downregulating a gene, each being present at a concentration at which the antisense oligonucleotide compound is practically ineffective on its own to downregulate a gene it is directed against, the combination leading to significant downregulation of both genes that the antisense oligonucleotides are directed against and may also downregulate other related genes.

In one aspect, the present invention provides a pharmaceutical composition for treating and/or preventing disease associated with reduced cellular cAMP and/or elevated levels of at least one PDE, said composition comprising a pharmaceutically acceptable carrier and at least two antisense oligonucleotide compounds, each oligonucleotide compound being directed against at least a portion of a different target PDE-encoding gene, each oligonucleotide compound being capable of downregulating the target gene it is directed against, each oligonucleotide compound being present at a concentration at which it exhibits less than 20% inhibition of its target PDE gene, the combination exhibiting greater than 20% inhibition and at least doubling the inhibition of at least one of the target genes and optionally other related genes.

As one of skill in the art will appreciate, the combination of oligonucleotide compounds in accordance with the present invention at very low concentrations, for example, concentrations with exhibit less than 1% inhibition of a target PDE gene, may not combine to exhibit an inhibition of at least 20%. The lowest concentration at which each oligonucleotide compound can be used to form a combination in accordance with the present invention will vary, and this concentration may be that at which 0.5% inhibition is achieved, or that concentration at which 1% to 5% inhibition is achieved.

The present invention provides a pharmaceutical composition for treating and/or preventing a disease associated with reduced cellular cAMP and/or elevated levels of at least one PDE, said composition comprising a pharmaceutically acceptable carrier and at least two antisense oligonucleotides that are each capable of downregulating a different target gene, at least one of the oligonucleotides being present at a concentration at which it is practically ineffective on its own, e.g. a concentration exhibiting less than 20% inhibition of the target gene, the combination of the oligonucleotides exhibiting more than 20% inhibition and at least doubling the inhibition of at least one of the target genes. and optionally other related genes.

The present invention further provides the use of a combination of at least two antisense oligonucleotide compounds for treating and/or preventing disease associated with reduced cellular cAMP, such as respiratory inflammatory disease, each oligonucleotide compound being directed against a gene coding for a different PDE isotype, each oligonucleotide compound being capable of downregulating the gene it is directed against, the oligonucleotide compounds being present at a concentration at which each oligonucleotide is practically ineffective on its own to downregulate the gene it is directed against, the combination of the at least two oligonucleotide compounds being effective to downregulate at least one of the genes the oligonucleotide compounds are directed against and optionally other related genes.

The present invention further provides a method of treating and/or preventing disease associated with reduced cellular cAMP, such as inflammatory respiratory disease, the method comprising administering to a subject at least two antisense oligonucleotide compounds each being capable of downregulating a different target PDE gene, the oligonucleotide compounds being administered at a concentration at which each oligonucleotide compound is practically ineffective on its own to downregulate its target gene, for example, a concentration exhibiting less than 20% inhibition of the target gene, the combination of the oligonucleotide compounds being effective to downregulate at least one of the genes the oligonucleotide compounds are directed against and optionally other related genes.

The present invention further provides the use of a pharmaceutical composition as described above for the manufacture of a medicament for the treatment and/or prevention of a disease associated with reduced cellular cAMP or increased cAMP-specific PDE levels (PDE-related disease) such as inflammatory disease. Inflammatory disease to which the present methods and compositions are directed is generally defined as diseases in which inflammatory cells and/or mediators are present. Examples of inflammatory diseases include, but are not limited to, multiple sclerosis, contact dermatitis, allergic and non-allergic eye diseases, rheumatoid arthritis, septic shock, osteoporosis and cognitive disorders. Inflammatory respiratory disease to which the present methods and compositions are directed is generally defined as diseases of the respiratory tract and lungs in which inflammatory cells and mediators are present. Examples of inflammatory respiratory disease include, but are not limited to, COPD, asthma, eosinophilic cough, bronchitis, acute and chronic rejection of lung allograft, sarcoidosis, pulmonary fibrosis, rhinitis and sinusitis.

The present invention further provides the use of a pharmaceutical composition as described above for the manufacture of a medicament for the treatment and/or prevention of a disease where decreased cyclic AMP is involved in the physiopathology.

The present invention further provides methods for modifying antisense oligonucleotides so that it may reach the target nucleotide and/or be more effective against the target gene for the treatment and/or prevention of inflammatory respiratory diseases.

The present invention further provides a formulation, including the composition described above, the formulation being systemic and/or topical.

The present invention further provides an in vivo method of delivering a pharmaceutical composition to a target polynucleotide, comprising administering to a subject the composition as described above in combination with a surfactant that permits the composition to reach the target gene(s).

Preferably, the subjects or patients that may be treated using the antisense oligonucleotide compounds of the present invention include, but are not limited to, invertebrates, vertebrates, birds, mammals such as pigs, goats, sheep, cows, dogs, cats, and particularly humans. Oligonucleotide compounds in accordance with the present invention are designed to be appropriate to the particular animal to be treated. In particular, the sequence of the antisense oligonucleotide compounds will vary with the subject being treated given interspecies genome differences.

The present invention further provides antisense oligonucleotides effective against, e.g. capable of inhibiting the expression of, the PDE family of enzymes, including, but not limited to, PDE3, PDE4 and PDE7. As will be appreciated by one of skill in the art, each PDE subtype may also includes isotypes. For example, PDE3 subtype include the PDE3A and PDE3B isotypes; the PDE4 subtype includes isotypes PDE4A, PDE4B, PDE4C and PDE4D; and the PDE7 subtype includes isotypes PDE7A1, PDE7A2, PDE7A3 and PDE7B.

When used herein the term "concentration at which the antisense oligonucleotide compound is practically ineffective" refers to the use of each oligonucleotide compound, when taken alone, at a concentration at which practically no downregulation is observed for the gene against which the oligonucleotide compound is directed (at a concentration at which less than 20% inhibition of the target gene is exhibited). This is in contrast to the effect of the combination of at least two oligonucleotide compounds in accordance with the present invention, each present at a concentration at which they are ineffective alone to downregulate the gene they are directed against (at a concentration at which less than 20% inhibition is exhibited), this combination exhibiting greater than 20% inhibition and being effective to at least double the inhibition of at least one of the genes against which the oligonucleotide compounds are directed.

The comparison of effectiveness of a single oligonucleotide is illustrated in, but not limited to, FIGS. 13 and 14 and table 4b and 5. For example in FIG. 13 A TOP 2430 which is directed against mouse PDE4B inhibits in vivo PDE4A, 4B, 4D and 7A but has no effect on PDE3B.

The comparison of effectiveness of combinations of at least 2 oligonucleotide compounds is illustrated in, but not limited to, FIGS. 9, 10, 11 and 12. For example in FIG. 9 the combination of Top-1703 (Seq ID No. 2) and Top-1301 (SEQ. ID NO.: 10) or Top-1706 (SEQ. ID NO.: 3) and Top-1303 (SEQ. ID NO.: 12) show a greater effect at decreasing expression of both PDE3A and PDE7A than either of the oligonucleotides had on either PDE3A or PDE7A expression when used alone. In FIG. 11 the combination of Top-1360 (SEQ. ID NO.: 19) and Top-1437 (SEQ. ID NO.: 28) or Top-1360 (SEQ. ID NO.: 19) and Top-1498 (SEQ. ID NO.: 36) or Top-1413 (SEQ. ID NO.: 23) and Top-1498 (SEQ. ID NO.: 36) or Top-1437 (SEQ. ID NO.: 28) and Top-1498 (SEQ. ID NO.: 36), show a greater effect at decreasing TNF-alpha expression and release in human PBMC than either of the oligonucleotides had on TNF-alpha when used alone. In FIG. 12 in vivo nasal instillation of mice with the combination of Top-2437 (PDE4B) and Top-2713 (PDE7A) show a greater effect at decreasing both mouse PDE4B and PDE7A expression than either of the oligonucleotides had on either PDE4B or PDE7A expression when used alone at low concentrations.

Many combinations of antisense oligonucleotide compounds may be used in accordance with the present invention, the combinations leading to multiple gene knock down as described above. Examples of combinations of antisense oligonucleotides may include, but are not limited to, at least one oligonucleotide compound directed against PDE3 with at least one oligonucleotide compound directed against PDE7. An alternative example of a combination may include at least one oligonucleotide directed against PDE4 and at least one oligonucleotide directed against PDE7. An alternative example of a combination may include at least one oligonucleotide directed against PDE3, at least one oligonucleotide directed against PDE4 and at least one oligonucleotide directed against PDE7. Such antisense oligonucleotide compounds may be chosen from, but are not limited to, the oligonucleotides provided in Tables 1a-f.

The term "oligonucleotide" as used herein refers to a nucleic acid molecule comprising from about 1 to about 100 nucleotides, more preferably from 1 to 80 nucleotides, and even more preferably from about 4 to about 35 nucleotides. The term "oligonucleotide" also includes modified oligonucleotides and oligonucleotide compounds as set out above.

The terms "modified oligonucleotide" and "modified nucleic acid molecule" as used herein refer to nucleic acids, including oligonucleotides, with one or more chemical modifications at the molecular level of the natural molecular structures of all or any of the nucleic acid bases, sugar moieties, internucleoside phosphate linkages, as well as molecules having added substituents, such as diamines, cholesteryl or other lipophilic groups, or a combination of modifications at these sites. The internucleoside phosphate linkages can be phosphodiester, phosphotriester, phosphoramidate, siloxane, carbonate, carboxymethylester, acetamidate, carbamate, thioether, bridged phosphoranidate, bridged methylene phosphonate, phosphorothioate, methylphosphonate, phosphorodithioate, bridged phosphorothioate and/or sulfone internucleotide linkages, or 3'-3', 2'-5' or 5'-5' linkages, and combinations of such similar linkages (to produce mixed backbone modified oligonucleotides). The modifications can be internal (single or repeated) or at the end(s) of the oligonucleotide molecule and can include additions to the molecule of the internucleoside phosphate linkages, such as cholesteryl, diamine compounds with varying numbers of carbon residues between amino groups and terminal ribose, deoxyribose and phosphate modifications which cleave or cross-link to the opposite chains or to associated enzymes or other proteins. Electrophilic groups such as ribose-dialdehyde may be covalently linked with an epsilon amino group of the lysyl-residue of such a protein. A nucleophilic group such as n-ethylmaleimide tethered to an oligomer could covalently attach to the 5' end of an mRNA or to another electrophilic site. The term modified oligonucleotides also includes oligonucleotides comprising modifications to the sugar moieties such as 2'-substituted ribonucleotides, or deoxyribonucleotide monomers, any of which are connected together via 5' to 3' linkages. Modified oligonucleotides may also be comprised of PNA or morpholino modified backbones where target specificity of the sequence is maintained.

Optionally, the presently described oligonucleotides may be formulated with a variety of physiological carrier molecules. The presently described oligonucleotides may also be complexed with molecules that enhance their ability to enter the target cells. Examples of such molecules include, but are not limited to, carbohydrates, polyamines, amino acids, peptides, lipids, and molecules vital to cell growth. For example, the oligonucleotides may be combined with a lipid, the resulting oligonucleotide/lipid emulsion, or liposomal suspension may, inter alia, effectively increase the in vivo half-life of the oligonucleotide.

Alternatively, oligonucleotides directed at PDE targets may also be protonated/acidified to function in a dual role as phosphodiesterase inhibitors and antibacterial agents. Accordingly, another embodiment of the presently described invention is the use of a PDE modulating therapeutic oligonucleotide that is additionally protonated/acidified to increase cellular uptake, improve encapsulation in liposomes, so it can also serve as an antibiotic. Additionally, the oligonucleotide may be complexed with a variety of well established compounds or structures that, for instance, further enhance the in vivo stability of the oligonucleotide, or otherwise enhance its pharmacological properties (e.g., increase in vivo half-life, reduce toxicity, etc.).

The term "nucleic acid backbone" as used herein refers to the structure of the chemical moiety linking nucleotides in a molecule. This may include structures formed from any and all means of chemically linking nucleotides. A modified backbone as used herein includes modifications to the chemical linkage between nucleotides, as well as other modifications that may be used to enhance stability and affinity, such as modifications to the sugar structure. For example an [alpha]-anomer of deoxyribose may be used, where the base is inverted with respect to the natural [beta]-anomer. In a preferred embodiment, the 2'-OH of the sugar group may be altered to 2'-O-alkyl or 2'-O-alkyl-n(O-alkyl), which provides resistance to degradation without comprising affinity.

The term "acidification" and "protonation/acidification" as used interchangeably herein refers to the process by which protons (or positive hydrogen ions) are added to proton acceptor sites on a nucleic acid. The proton acceptor sites include the amine groups on the base structures of the nucleic acid and the phosphate of the phosphodiester linkages. As the pH is decreased, the number of these acceptor sites which are protonated increases, resulting in a more highly protonated/acidified nucleic acid.

The term "protonated/acidified nucleic acid" refers to a nucleic acid that, when dissolved in water at a concentration of approximately 16 A260 per ml, has a pH lower than physiological pH, i.e., lower than approximately pH 7. Modified nucleic acids, nuclease-resistant nucleic acids, and antisense nucleic acids are meant to be encompassed by this definition. Generally, nucleic acids are protonated/acidified by adding protons to the reactive sites on a nucleic acid, although other modifications that will decrease the pH of the nucleic acid can also be used and are intended to be encompassed by this term.

The term "end-blocked" as used herein refers to a nucleic acid with a chemical modification at the molecular level that prevents the degradation of selected nucleotides, e.g., by nuclease action. This chemical modification is positioned such that it protects the integral portion of the nucleic acid, for example the coding region of an antisense oligonucleotide. An end block may be a 3' end block or a 5' end block. For example, a 3' end block may be at the 3'-most position of the molecule, or it may be internal to the 3' ends, provided it is 3' of the integral sequences of the nucleic acid.

The term "substantially nuclease resistant" refers to nucleic acids that are resistant to nuclease degradation, as compared to naturally occurring or unmodified nucleic acids. Modified nucleic acids of the invention are at least 1.25 times more resistant to nuclease degradation than their unmodified counterpart, more preferably at least 2 times more resistant, even more preferably at least 5 times more resistant, and most preferably at least 10 times more resistant than their unmodified counterpart. Such substantially nuclease resistant nucleic acids include, but are not limited to, nucleic acids with modified backbones such as phosphorothioates, methylphosphonates, ethylphosphotriesters, 2'-0-methylphosphorothioates, 2'-O-methyl-p-ethoxy ribonucleotides, 2'-O-alkyls, 2'-O-alkyl-n(O-alkyl), 3'-O-alkyls, 3'-O-alkyl-n(O-alkyl), 2'-fluoros, 2'-deoxy-erythropentofuranosyls, 2'-O-methyl ribonucleosides, methyl carbamates, methyl carbonates, inverted bases (e.g., inverted T's), or chimeric versions of these backbones.

The term "substantially acid resistant" as used herein refers to nucleic acids that are resistant to acid degradation as compared to unmodified nucleic acids. Typically, the relative acid resistance of a nucleic acid will be measured by comparing the percent degradation of a resistant nucleic acid with the percent degradation of its unmodified counterpart (i.e., a corresponding nucleic acid with "normal" backbone, bases, and phosphodiester linkages). A nucleic acid that is acid resistant is preferably at least 1.5 times more resistant to acid degradation, at least 2 times more resistant, even more preferably at least 5 times more resistant, and most preferably at least 10 times more resistant than their unmodified counterpart.

The terms "PDE3A, PDE3B, PDE4A, PDE4B, PDE4C, PDE4D, PDE7A, PDE7B oligonucleotide" as used herein each refer to an oligonucleotide that is targeted, respectively, to sequences that affect PDE3A, PDE3B, PDE4A, PDE4B, PDE4C, PDE4D, PDE7A, PDE7B expression or activity. These include, but are not limited to, PDE3A, PDE3B, PDE4A, PDE4B, PDE4C, PDE4D, PDE7A, PDE7B DNA coding sequences, PDE3A, PDE3B, PDE4A, PDE4B, PDE4C, PDE4D, PDE7A, PDE7B DNA promoter sequences, PDE3A, PDE3B, PDE4A, PDE4B, PDE4C, PDE4D, PDE7A, PDE7B DNA enhancer sequences, mRNA encoding PDE3A, PDE3B, PDE4A, PDE4B, PDE4C, PDE4D, PDE7A, PDE7B, and the like.

As discussed above, one embodiment of the present invention provides antisense oligonucleotides targeted to sequences that affect PDE3A, PDE3B, PDE4A, PDE4B, PDE4D, PDE7A, expression or activity. In one embodiment the antisense oligonucleotides may have one of the sequences identified in Tables 1a-f. In another embodiment, the antisense oligonucleotide may comprise fragments or variants of these sequences, as will be understood by a person skilled in the art, that may alter the oligonucleotide make-up and/or length, but which maintains or increases the activity of the oligonucleotide to downregulate gene expression. In another embodiment the present invention provides for combinations of at least two antisense oligonucleotides having the sequences identified in Tables 1a-f.

The terms "treatment", "treating", "therapy" and the like are used herein to generally mean obtaining a desired pharmacologic and/or physiological effect. The effect may be prophylactic in terms of completely or partially preventing a disease or symptom thereof and/or may be therapeutic in terms of a partial or complete cure for a disease and/or amelioration of an adverse effect attributable to the disease. "Treatment" as used herein covers any treatment of a disease in a subject as previously defined, particularly a human, and includes:

(a) preventing a disease from occurring in a subject which may be predisposed to the disease but has not yet been diagnosed as having it;
(b) inhibiting a disease, i.e., arresting its development; or
(c) relieving a disease, i.e., causing regression of the disease.

The term "pharmaceutically acceptable" as it is used herein with respect to carriers, surfactants and compositions refers to substances which are acceptable for use in the treatment of a subject patient that are not toxic or otherwise unacceptable for administration by any of the routes herein described.

The invention is generally directed toward the treatment of subjects by the administration of therapeutically effective amounts of antisense oligonucleotide compounds in accordance with the present invention, including siRNA, ribozymes, short nucleotide sequences as single or double stranded including RNA and/or DNA that may be complementary to a target nucleic acid, or may optionally be modified as described above, an RNA oligonucleotide having at least a portion of said RNA oligonucleotide capable of hybridizing with RNA to form an oligonucleotide-RNA duplex, or a chimeric oligonucleotide, that will downregulate or inhibit the expression of an endogenous gene in vivo.

By "therapeutically effective" amount is meant a nontoxic but sufficient amount of an antisense oligonucleotide compound to provide the desired therapeutic effect. In the present case, that dose of antisense oligonucleotide compound effective to relieve, ameliorate, or prevent symptoms of the condition or disease being treated, e.g. disease associated with reduced cellular cAMP, PDE-related disease, inflammatory disease such as inflammatory respiratory disease.

The pharmaceutical compositions provided herein comprise antisense oligonucleotide compounds described above and one or more pharmaceutically acceptable surfactants. Suitable surfactants or surfactant components for enhancing the uptake of the antisense oligonucleotides of the invention have been previously described in U.S. Application Publication No. 2003/0087845, the contents of which are incorporated with respect to surfactants The application states that suitable surfactants " . . . include synthetic and natural as well as full and truncated forms of surfactant protein A, surfactant protein B, surfactant protein C, surfactant protein D and surfactant protein E, di-saturated phosphatidylcholine (other than dipalmitoyl), dipalmitoylphosphatidylcholine, phosphatidylcholine, phosphatidylglycerol, phosphatidylinositol, phosphatidylethanolamine, phosphatidylserine; phosphatidic acid, ubiquinones, lysophosphatidylethanolamine, lysophosphatidylcholine, palmitoyl-lysophosphatidylcholine, dehydroepiandrosterone, dolichols, sulfatidic acid, glycerol-3-phosphate, dihydroxyacetone phosphate, glycerol, glycero-3-phosphocholine, dihydroxyacetone, palmitate, cytidine diphosphate (CDP) diacylglycerol, CDP choline, choline, choline phosphate; as well as natural and artificial lamelar bodies which are the natural carrier vehicles for the components of surfactant, omega-3 fatty acids, polyenic acid, polyenoic acid, lecithin, palmitinic acid, non-ionic block copolymers of ethylene or propylene oxides, polyoxypropylene, monomeric and polymeric, polyoxyethylene, monomeric and polymeric, poly (vinyl amine) with dextran and/or alkanoyl side chains, Brij 35, Triton X-100 and synthetic surfactants ALEC, Exosurf, Survan and Atovaquone, among others. These surfactants may be used either as single or part of a multiple component surfactant in a formulation, or as covalently bound additions to the 5' and/or 3' ends of the antisense oligonucleotides (oligos)."

The antisense component of the present compositions, which includes the combination of at least two antisense oligonucleotide compounds, may be contained in a pharmaceutical formulation within a lipid particle or vesicle, such as a liposome or microcrystal. As described in U.S. Pat. No. 6,025,339, the lipid particles may be of any suitable structure, such as unilamellar or plurilamellar, so long as the antisense oligonucleotide is contained therein. Positively charged lipids such as N-[1-(2,3-dioleoyloxi) propyl]-N,N,N-trimethylammoniumethylsulfate, or "DOTAP," are particularly preferred for such particles and vesicles. The preparation of such lipid particles is well known. See, e.g., U.S. Pat. Nos. 4,880,635 to Janoff et al.; 4,906,477 to Kurono et al.; 4,911,928 to Wallach; 4,917,951 to Wallach; 4,920,016 to Allen et al.; 4,921,757 to Wheatley et al.; etc.

The composition of the invention may be administered by any means that transports the antisense oligonucleotide compound to the desired site, such as the lung. The antisense compounds disclosed herein may be administered to the lungs of a patient by any suitable means, but are preferably administered by inhalation of an aerosol comprised of respirable particles that comprise the antisense compound.

The composition of the present invention may be administered into the respiratory system as a formulation including particles of respirable size, e.g. particles of a size sufficiently small to pass through the nose, mouth and larynx upon inhalation and through the bronchi and alveoli of the lungs. In general, respirable particles range from about 0.5 to 10 microns in size. Particles of non-respirable size that are included in the aerosol tend to deposit in the throat and be swallowed, and the quantity of non-respirable particles in the aerosol is preferably thus minimized. For nasal administration, a particle size in the range of 10-500 micro-M (micrometer)) is preferred to ensure retention in the nasal cavity.

Liquid pharmaceutical compositions of active compound (the antisense oligonucleotide compound(s)) for producing an aerosol may be prepared by combining the antisense compound with a suitable vehicle, such as sterile pyrogen free water or phosphate buffered saline.

A solid particulate composition comprising the antisense compound may optionally contain a dispersant that serves to facilitate the formation of an aerosol as well as other therapeutic compounds. A suitable dispersant is lactose, which may be blended with the antisense compound in any suitable ratio, e.g., a 1 to 1 ratio by weight.

The antisense compositions may be administered in an anti-bronchoconstriction, anti-allergy(ies) and/or anti-inflammatory effective amount, which amount depends upon the degree of disease being treated, the condition of the subject patient, the particular formulation, the route of administration, the timing of administration to a subject, etc. In general, intracellular concentrations of the oligonucleotide of from 0.05 to 50.micro.M, or more particularly 0.2 to 5.micro.M, are desirable. For administration to a mammalian patient such as a human, a dosage of about 0.001, 0.01, 0.1, or 1 mg/Kg up to about 50, or 100 mg/Kg or more is typically employed. However, other doses are also contemplated. Depending on the solubility of the active compound in any particular formulation, the daily dose may be divided among one or several unit dose administrations.

The aerosols of liquid particles comprising the antisense compound may be produced by any suitable means, such as with a nebulizer. Nebulizers are commercially available devices that transform solutions or suspensions of the active ingredient into a therapeutic aerosol mist either by means of acceleration of a compressed gas, typically air or oxygen, through a narrow venturi orifice or by means of ultrasonic agitation. Suitable formulations for use in nebulizers comprise the active antisense oligonucleotide ingredient in a liquid carrier in an amount of up to 40% w/w preferably less than 20% w/w of the formulation. The carrier is typically water or a dilute aqueous alcoholic solution, preferably made isotonic with body fluids by the addition of, for example, sodium chloride. Optional additives include preservatives if the formulation is not prepared sterile, for example, methyl hydroxybenzoate, anti-oxidants, anti-bacterials, flavorings, volatile oils, buffering agents and emulsifiers and other formulation surfactants.

The aerosols of solid particles comprising the active oligonucleotide compound(s) and a pharmaceutically acceptable surfactant may likewise be produced with any solid particulate medicament aerosol generator. Aerosol generators for administering solid particulate medicaments to a subject produce particles that are respirable, as explained above, and generate a volume of aerosol containing a predetermined metered dose of a medicament at a rate suitable for human administration. The active oligonucleotide ingredient typically comprises from 0.1 to 100 w/w of the formulation. A second type of illustrative aerosol generator comprises a metered dose inhaler. Metered dose inhalers are pressurized aerosol dispensers, typically containing a suspension or solution formulation of the active ingredient in a liquified propellant. During use these devices discharge the formulation through a valve adapted to deliver a metered volume, typically from 10 to 150 .mu.l, to produce a fine particle spray containing the active ingredient. Suitable propellants include certain chlorofluorocarbon compounds, for example, dichlorodifluoromethane, trichlorofluoromethane, dichlorotetrafluoroethane or hydrofluoroalkanes and mixtures thereof. The formulation may additionally contain one or more cosolvents, for example, ethanol, emulsifiers and other formulation surfactants, such as oleic acid or sorbitan trioleate, anti-oxidants and suitable flavoring agents.

The aerosol, whether formed from solid or liquid particles, may be produced by the aerosol generator at a rate of from about 1 to 150 liters per minute.

The formulations of the present invention may be oral, intrabuccal, intrapulmonary, rectal, intrauterine, intratumor, intracranial, nasal, intramuscular, subcutaneous, intravascular, intrathecal, inhalable, transdermal, intradermal, intracavitary, implantable, iontophoretic, ocular, vaginal, intraarticular, otical, intravenous, intramuscular, intraglandular, intraorgan, intralymphatic, implantable, slow release or enteric coating formulations. The carriers used in the formulations may be, for example, solid and/or liquid carriers.

Reference may be made to "Remington's Pharmaceutical Sciences", 17th Ed., Mack Publishing Company, Easton, Pa., 1985, for other carriers that would be suitable for combination with the present oligonucleotide compounds to render compositions/formulations suitable for administration to treat respiratory disease.

In a further aspect of the present invention, an article of manufacture is provided which includes packaging material contained within which is a pharmaceutically acceptable antisense oligonucleotide composition that is therapeutically effective to treat conditions associated with reduced cellular cAMP, or elevated levels of PDE, including inflammatory disease. In one embodiment, the composition comprises an antisense oligonucleotide compound that is effective to inhibit a PDE gene, said oligonucleotide compound being at least 50% complementary to the gene. In another aspect, the composition comprises at least 2 antisense oligonucleotide compounds, each antisense oligonucleotide compound being capable of downregulating a different PDE gene, each antisense oligonucleotide compound being present at a concentration at which the antisense oligonucleotide compound is practically ineffective on its own to down-regulate the gene it is directed against, the combination of the antisense oligonucleotide compounds being effective to downregulate at least one of the genes that the antisense oligonucleotides are directed against.

In one embodiment, the packaging material of the article comprises a label which indicates that the composition can be used to treat inflammatory disease and may additionally include an indication that the disease is one of multiple sclerosis, contact dermatitis, allergic and non-allergic eye diseases, rheumatoid arthritis, septic shock, osteoporosis and cognitive disorders.

In another embodiment, the packaging material of the article comprises a label which indicates that the composition can be used to treat inflammatory respiratory disease, and may additionally include an indication that the disease is one of COPD, asthma, eosinophilic cough, bronchitis, acute and chronic rejection of lung allograft, sarcoidosis, pulmonary fibrosis, rhinitis or sinusitis.

For the purposes of the present invention, the packaging material may be any suitable material for packaging a nucleotide-containing composition in accordance with the present invention, including a bottle or other container (either plastic or glass), a carton, a tube, or other protective wrapping. As will be appreciated, the packaging may vary with the nature of the oligonucleotide composition, for example, a liquid formulation may be packaged differently than an aerosol formulation.

The present invention is illustrated in further detail by the following non-limiting examples.

Materials and Reagents

RPMI 1640 (Wisent, cat# 10040 CV); FBS (Fetal Bovine Serum, Wisent, cat# 80150); Penicillin, Streptomycin (GIBCO, cat# 15140-122); HEPES (Wisent, cat# 26060CI) and L-glutamine (Gibco, cat# 25030-081); DMEM/F12 (Wisent, cat# 10090CV); Sodium Pyruvate (Wisent, cat# 25000-Ci); PBS Sterile (GIBCO, cat# 25030-081); Trypsin 0.25% and EDTA 0.01% (Wisent, cat# 25-052-Ci); Hanks Balanced Salt Solution (HBSS) cellgro, cat#20021-cv; PHA (Phytohemaglutinin, Sigma, cat#L-9132, lot#: 073K8925) hEGF (human recombinant epidermal growth factor, cat-4230; BPE: clonetics cat#4009; hydrocortisone: clonetics cat#4031; epinephrine: clonetics cat#4221; transferring: clonetics cat#4205; insulin: clonetics cat#4021; retinoic acid: clonetics cat#4085; triiodothyronine: clonetics cat#4211; gentamicin/amphotericinB: clonetics cat#4081; human epithelial growth factor (hEGF): clonetics cat#4230; Insulin, cat# cc-4021; hFGF (human fibroblast growth factor) cat# cc-4068; SmBm Bullet kits (Cat# CC 3182, Clonetics). BEBM Bullet kits (Cat# CC 4175, Clonetics); Trizol: Invitrogen, cat#15596-018Dnase I: Fermentas, cat#EN0521; Superscript First-Strand Synthesis System for RT-PCR kit (Invitrogen, cat#11904-018); dNTPs: Invitrogen, cat# 10297-018; oligo $(dT)_{12-18}$: Invitrogen, cat#11904-018; Qiagen RNAeasy Mini Kit (Qiagen, Cat#74106); β-Mercaptoethanol (Sigma, Cat#M-6250); • 99% Ethanol (Commercial alcohols Inc., Brampton, Ontario, Canada); • QiaVac 24 Manifold (Qiagen, Cat#19403); •

Disposable Vacconnectors (Qiagen, Cat#19407); • DNAse I kit (Fermentas, Cat.# EN0521); • RiboGreen Quantification Reagent (Invitrogen-Molecular probes, Cat # R-11490); Taq PCR core kit (Qiagen, cat#201223), • Light-Cycler Instrument version 1.5 (Roche, Cat# 3531414); • LC Capillaries for 20 ml reactions (Roche, cat# 1909339); • LC FastStart DNA Master SYBR Green 1 PLUS (100 ml) (Roche, Cat# 03752186001); K3EDTA tubes (Greiner Bio-one, cat#: 455036B110306); Ficoll (Amersham Biosciences; cat#: 17-1440-03); Human TNF-alpha ELISA kit, (BioSource Cat#CHC-1754, lot# 041703); Mouse TNF-alpha ELISA kit (BioSource, cat#cmc3013); ELISA plate reader (filter 450 nm, reference filter 650 nm, Biorad, model 680); Escort II transfection reagent, (Sigma, cat#L6037), Lipopolysaccharide (SIGMA-Aldrich; cat.#L-4391, lot # 083K4048, *E. Coli* 0111:B4); Xylazine (Anased), (Novopharm; cat.#02239093; lot no. KA09802D); Ketamine (Vetalar), (Bioniche; cat.#01989529; lot.#K033A); Hema-3 stain set (Fisher scientific Co. Cat#122-911, lot#999901); Polytron PT 1200 (Brinkmann Instruments); Alamar Blue, (Biosource cat#DAL1100), Human Lung Total RNA, (BD Bioscience, cat#64092-1, lot#4030253); Human smooth muscle total RNA, (BD Bioscience, cat#cr2628, lot#3110321); Human brain total RNA, (BD Bioscience, cat#64098-1, lot#4010842).

Cells

Human Bronchial smooth muscle cells (BSMC) (cat# CC 2576); normal human bronchial epithelial cells (NHBE) (cat# CC 2540) were purchased from Clonetics. EOL-1 (Human acute myeloid "Eosinophilic" leukemia cell line; ATCC). U937 (Human histiocytic cell line; ATCC), HL-60 (Human acute promyelocytic leukemia cell line; ATCC); A549 (Human lung carcinoma cell lines; ATCC); Jurkat (Human acute T cell leukemia; ATCC) and Hut-78 (Human cutaneous T lymphocyte lymphoma cell lines; ATCC). NCI—H292 (Human mucoepidermoid pulmonary carcinoma cell line, ATCC); PBMC, (Human peripheral blood mononuclear cells).

Cell Culture

EOL-1, U937, HL-60, Jurkat and NCI—H292 were cultured in RPMI 1640 with 2 mM L-glutamine; 1.5 g/L sodium bicarbonate; 4.5 g/L glucose; 10 mM Hepes; 1 mM sodium pyruvate; 10% FBS, Penicillin 100 U/mL, Streptomycin 100 microg/mL.

Hut78 were cultivated in Iscove's modified medium with 4 mM L-glutamine; 1.5 g/L sodium bicarbonate; 10% FBS, Penicillin 100 U/mL, Streptomycin 100 mcg/mL.

A549 were cultivated in Ham's F12K with 2 mM L-glutamin; 1.5 g/L sodium bicarbonate; 10% FBS, Penicillin 100 U/mL, Streptomycin 100 microg/mL.

Bronchial smooth muscle cells were cultured in 25 $cm^2$ flasks with SmBm medium which contains: 0.5 microg/mL hEGF; 25 mg/ml gentamicin; 25 microg/mL Amphotericin B; 2.5 mg/mL Insulin; hFGF 10 nanog/mL and FBS 5%. Cell culture was performed for 10 days in order to obtain enough cells for each experiment.

Normal human bronchial epithelial cells (NHBE) were cultured in 25 $cm^2$ flasks with BEBM medium that contained basal medium (500 mL) and the following growth supplements: BPE: 2 mL; Hydrocortisone: 0.5 mL; hEGF: 0.5 mL; Epinephrine: 0.5 mL; Transferrin: 0.5 mL; Insulin: 0.5 mL; Retinoic Acid: 0.5 mL; Triiodothyronin: 0.5 mL; GA-1000: 0.5 mL. Cell culture was performed for 10 days in order to obtain enough cells for each experiment.

Cell Viability

Cell viability was systematically assayed using Alamar Blue test as suggested by the manufacturer.

Human Peripheral Blood Mononuclear Cells (PBMC)

PBMC were isolated by Ficoll-Hypaque density gradient centrifugation of EDTA K3 blood from normal donors. PBMC were plated at $2\times10^6$ cells/mL/well in 12 well plates in RPMI 1640 cell culture medium supplemented with 10% heat inactivated FBS, Penicillin 100 U/mL, Streptomycin 100 microg/mL.

Antisense Treatment U937, EOL-1, Jurkat, Hut-78 Cell Lines:

Cells were harvested by centrifugation (5 minutes, 1500 RPM, at room temperature), washed with 1×HBSS and re-suspended at $1\times10^6$ cells/ml in RPMI medium without serum. $1\times10^6$ cells were incubated for 5 minutes with an exact anti-sense concentration (between 0 and 20 microM) in a sterile microtube. Each reaction was then transferred in 12 well plates and incubated at 37° C. for 5 hours. RPMI/FBS 20% was added to a final concentration of 10% FBS and cells were incubated at 37° C. overnight. Cells were harvested by centrifugation (5 minutes, 1500 RPM, at room temperature) and washed with 1× Hans Balanced Salt Solution (HBSS).

A549 Cell Line (Direct Transfection):

Cells were trypsinized, re-suspended in DMEM-F12 medium ($10^6$ cells/well) and incubated at 37° C. overnight in serum deprivation conditions. The next day, adherent cells were incubated at 37° C. for 5 hours with antisense at different concentrations (0, 5, 10, 15 or 20 microM) directly in wells. DMEM-F12/FBS 20% was added to a final concentration of 10% FBS and cells were incubated at 37° C. overnight. Cells were harvested by centrifugation (5 minutes, 1500 RPM, at room temperature) and washed with 1×HBSS.

Escort II Reagent Mediated A549 Cell Line Transfection

A549 cells were seeded over night at $3\times10^5$ cells/mL in 12 well plates at 37° C., 5% $CO_2$. The day after, cells were washed twice with 1×HBSS and covered with 500 microL serum and antibiotics free DMEM-F12. Transfection complex consisted of 1 microg of antisense and 2.5 microL Escort II reagent. The DNA-Escort II complex was prepared and added to the cells according to recommendations of the manufacturer.

BSMC and NHBE Primary Cells:

The cells were trypsinized (trypsin 0.025%, EDTA 0.01%) for 3-5 minutes at 37° C., the reaction was stopped with culture medium, the cells counted resuspended at $5\times10^5$ cells/mL in 12 well plates and incubated at 37° C. (overnight). The next day, cells were washed, the medium changed and replaced with culture medium without serum. Antisense was added at different concentrations (between 0 and 20 microM) directly in the wells. The mixture was incubated at 37° C. for 5 hours. The serum was added to a final concentration of 5%, and the culture incubated for another 48 hours. The cells were washed with HBSS 3 times, harvested and RNA was extracted.

PBMC $2\times10^6$ cells/mL/well are incubated with antisense concentrations ranging from 0 to 5 microM in RPMI 1640 cell culture medium supplemented with 5% heat inactivated FBS, Penicillin 100 U/mL, Streptomycin 100 microg/mL and 10 microg/mL PHA for 16 to 20 hrs. After that cells are recovered and washed before RNA preparation.

RNA Extraction

RNA is extracted from cell pellets according to RNAeasy mini Kit protocol using the QiaVac 24 manifold from Qiagen and treated with DNase-I according to Fermentas procedures. RNA is quantified using the RiboGreen reagent according to the manufacturer protocol (Invitrogen-Molecular probes).

Reverse Transcription (RT)

Preparation of First-Strand cDNA was Performed Using the Superscript First-Strand Synthesis System for RT-PCR kit, in a total reaction volume of 20 microL. 1 microg of RNA was first denatured at 65° C. for 5 minutes, with 0.5 mM of each dNTPs, 0.5 microg of oligo $(dT)_{12-18}$ and chilled on ice for at least 1 min. The mixture was incubated at 42° C. for 2 minutes and a second pre-mix containing 1×First-Strand Buffer, 10 mM DTT, 40 units of RNaseOUT and 40 units of SuperScript II RT was added. Reactions were incubated at 42° C. for 10 minutes, at 50° C. for 1 hour and inactivated by heating at 70° C. for 15 minutes.

Polymerase Chain Reaction (PCR)

PCR was performed with optimized quantity of cDNA (10 to 200 nanog depending on the gene target) in 1×PCR buffer (10×: Tris-HCl, KCl, $(NH_4)_2SO_4$, 15 mM MgCl12; pH8.7)) in a total reaction volume of 50 microL, 0.2 mM of each dNTPs, 8.5 pmol of each PCR primer and 2.5 units of Taq DNA Polymerase. The mixture was heated at 94° C. for 5 minutes, followed by 30 to 35 cycles (depending on targets), each consisting of incubation for 1 minute at 94° C., 45 seconds at 60° C. and 45 seconds at 72° C. Supplemental elongation was performed at 72° C. for 10 minutes. PCR products were analyzed by 1.5% agarose gel electrophoresis in the presence of ethidium bromide. PCR primer sequences used for each gene and expected sizes of PCR amplification products are described in Tables 2a-b. Quantification of PCR products was performed using the Total Lab software (Background subtraction with Rolling Ball; Ultra Lum Inc., Model UC4800).

Real-time PCR

PCR reaction mixtures are prepared with 3 microL of cDNA reaction in a total volume of 20 microL in presence of 0.5 mM of each PCR primer and 4 microL of LC FastStart DNA Master SYBR Green 1 PLUS.

Step 1 (Denaturation): 95° C., 10 min (slope 20° C./sec)

Step 2 (Cycles×40): 95° C., (slope 20° C./sec); 57° C., 5 sec. (slope 20° C./sec) (Except for PDE4D Tm=59° C.); 72° C., 10 sec. (slope 20° C./sec)

Step 3 (Melting curve): 95° C., (slope 20° C./sec); 70° C., 30 sec. (slope 20° C./sec); 95° C., 0 sec. (slope 0.1° C./sec)

Step 4 (Cool): 40° C., 30 sec (slope 20° C./sec)

PCR primer sequences used for each gene are described in Tables 2c-d. Quantification of PCR products was performed using the RelQuant program (Roche).

Human TNF-alpha ELISA

PBMC are transfected with antisense(s) (0.05 microM each) as described before without PHA stimulation for 16-18 hrs. After that cells are stimulated with PHA (10 microg/mL) for 6 hrs. Supernatants are therefore collected, centrifuged 5 min at 2000 rpm, stored at −80° C. until used for ELISA as described by the manufacturer.

Animals.

All animal protocols were approved by the Mispro Biotech Services Inc. Animal Care Committee and conform to the Canadian Council of Animal Care guidelines regarding animal experimentation. C57BL/6 and AKR/J mice (20-25 g)

(Charles River Canada, Lasalle QC, Canada) were housed at Mispro Biotech Services Inc. animal facility (Montreal QC, Canada).

In vivo antisense targets validation and multiple gene cross knock down

C57BL/6 mice were lightly anesthetized by i.p. injection of ketamine/xylazine. For groups receiving the antisense oligonucleotides, mice were pre-treated by nasal instillation of the antisense oligonucleotide solution (50 mg/mouse/antisense) 16-20 hrs. before lungs harvesting. Control mice received an identical amount of control antisense oligonucleotide in sterile PBS.

Lipopolysaccharide(LPS)-induced Lung Inflammation Model.

C57BL/6 mice were lightly anesthetized by i.p. injection of ketamine/xylazine and acute lung inflammation was induced by nasal instillation of 10 mg of LPS from E. coli serotype 0111:B4 (Sigma-Aldrich, Oakville ON, Canada). Control mice receive a similar volume of sterile PBS. For groups receiving the antisense oligonucleotides, mice were pre-treated by nasal instillation of the antisense oligonucleotide solution (200 mg/mouse) 12 h before LPS exposure. Control mice received an identical amount of control antisense oligonucleotide in sterile PBS. Bronchoalveolar lavage and lung harvesting were performed 6 h after LPS instillation.

μμ

Cigarette Smoke-induced Lung Inflammation Model.

AKR/J mice were exposed to the whole smoke from eight 1R3F research cigarettes (University of Kentucky) using a smoking apparatus (SCIREQ Scientific Respiratory Equipment Inc., Montreal Canada). Control mice were sham smoked. For groups receiving the antisense oligonucleotides, mice were lightly anesthetized and were pre-treated by nasal instillation of the antisense oligonucleotide (200 mg/mouse) solution 3 h before and 24 h after cigarette smoke-exposure. Control mice received an identical amount of control antisense oligonucleotide in sterile PBS. Bronchoalveolar lavage and lung harvesting were performed 48 h after cigarette smoke exposure.

Bronchoalveolar Lavage (BAL) and Differential Cell Count.

Mice were anesthetized by i.p. injection of ketamine/xylazine. A tracheotomy was performed and the lungs were washed 4 times with 0.5 ml of ice-cold PBS. Total cells were counted and then centrifuged onto a cytospin slide. The differential cell count was assessed after cytospin slides were stained with Wright-Giemsa. At least 200 cells were counted under oil immersion microscopy. BAL fluids were stored at −80° C. for subsequent TNF-alpha measurements.

Mouse TNF-alpha ELISA.

Levels of TNF-alpha in BAL fluid were measured using a murine TNF-alpha ELISA kit according to the manufacturer recommendations.

Reverse Transcription (RT) and Real-Time PCR.

Mice Lungs were homogenized using a polytron PT 1200 (Brinkmann Instruments) and total RNA was extracted using the Qiagen RNAeasy mini kit (Qiagen, Mississauga ON, Canada) followed by DNase I digestion. Total RNA was quantified using the Ribogreen Fluorescent Assay (Invitrogen Corporation, Burlington ON, Canada). cDNA was prepared from 1 microg RNA using the First-Strand cDNA Synthesis Using SuperScript™ II RT kit (Invitrogen Corporation, Burlington ON, Canada). Real-time PCR reactions were prepared with 50 nanog cDNA using the LC FastStart DNA Master SYBR Green 1 PLUS (Roche Diagnostics, Laval QC, Canada) and run in a LightCycler (Roche Diagnostics, Laval QC, Canada). Primer sets were designed by TibMolbiol (Adelphia, N.J.) and GSP purified (see Table 2d). PBGD or HPRT were used as a reference gene. Each real-time PCR run included a calibrator cDNA (prepared from pooled RNA from mouse lung tissue) and gene/PBGD or gene/HPRT ratios were normalized using the Cp values of the calibrator. In addition, standard curves for each gene, for PBGD and for HPRT were done using a calibrator cDNA, and coefficient files were created to include correction for the differences in amplification efficiency between target and reference genes.

EXAMPLES

Example 1

Figure 1:
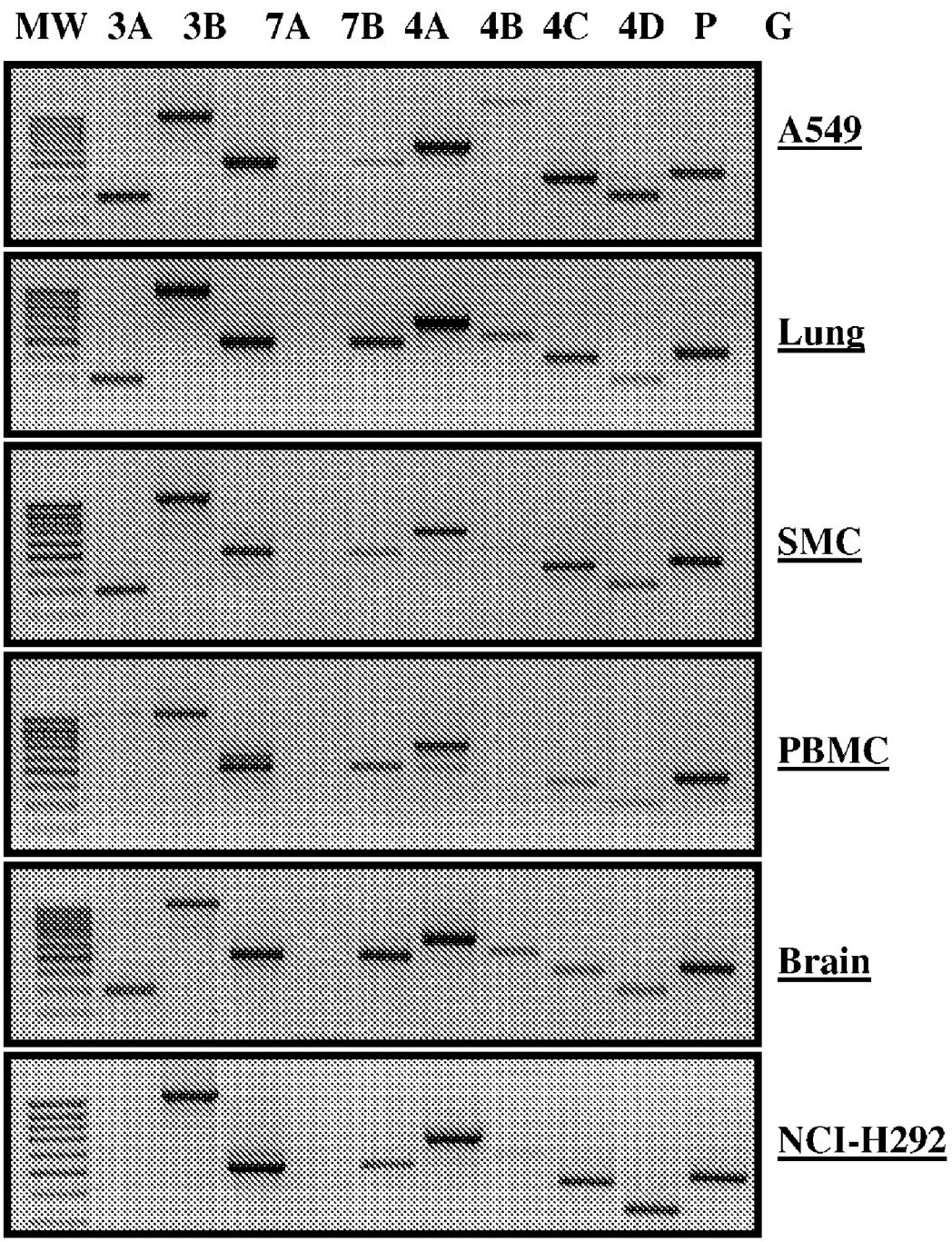
FIG. 1 illustrates 6 gels of semi-quantitative PCR showing the expression profile of different phosphodiesterases (PDEs) in structural (A549, bronchial smooth muscle cells (BSMC), NCI—H292); immune cells (peripheral blood mononuclear cells, PBMC) and in tissue (Lung, Brain). 3A=PDE3A; 3B=PDE3B; 7A PDE7A; 7B=PDE7B; 4A PDE4A; 4B=PDE4B; 4C=PDE4C; 4D=PDE4D; P=PBGD (PORPHOBILINOGEN DEAMINASE); G=GAPDH (Glyceraldehyde 3-phosphate dehydrogenase); (−)=Amplification of RNA without reverse transcription; MW=100 bp DNA ladder.
Figure 2:
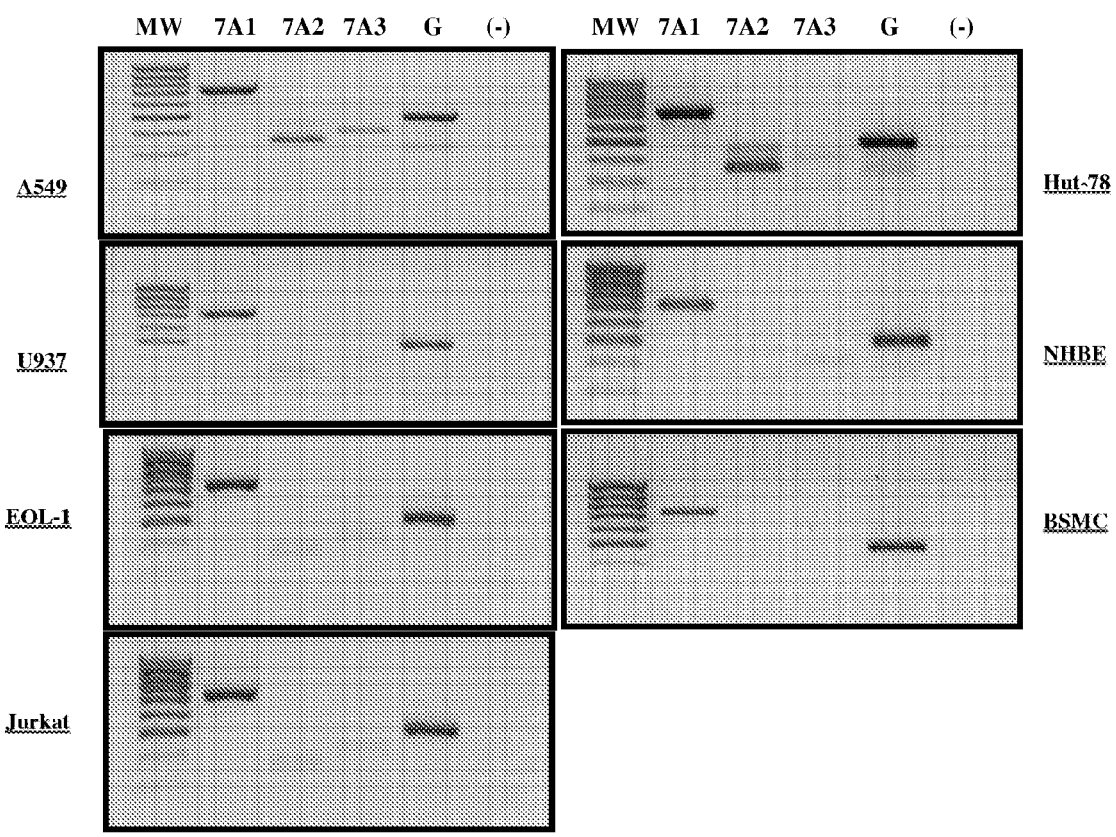
FIG. 2 illustrates 7 gels of semi-quantitative PCR showing the expression profile of PDE7A isotypes in structural (A549, NHBE, BSMC) and non-structural (Eol-1, Hut-78, Jurkat, and U937) cells that are related to potentially important cells in the lung inflammatory response. 7A1=PDE7A1; 7A2=PDE7A2; 7A3=PDE7A3; G=GAPDH, (−)=Amplification of RNA without reverse transcription and MW=100 bp DNA ladder.

This example relates to PDE Isotype cell and tissue distribution. Inflammatory respiratory diseases are characterized by an interaction between inflammatory cells (macrophages, lymphocytes, neutrophils and eosinophils) and tissue cells (mostly epithelial cells and smooth muscle cells). mRNA expression of the isotypes of PDE 3 (PDE3A and B), PDE 7 (PDE7A and B) and of PDE 4 (PDE4A, B, C, and D) in different cells and tissue was assessed. A summary of the primers used for every PDE isotype can be found in Table 2a. The cells that were chosen were A549 (epithelial cell from an adenocarcinoma of the lung), and NCI-H292 (mucoepidermoid pulmonary carcinoma). Expression in primary human cells was assessed in BSMC (Human bronchial smooth muscle cells) and PBMC (Peripheral blood mononuclear cells). Normal human lung was also used to characterize the expression of PDEs. Finally, normal human brain was included as a control, since most PDEs are expressed in this tissue. As can be seen in FIG. 1 different cells and tissues express different isotypes of PDEs except for PDE 7A and PDE4B that were expressed in every cell and tissue assessed under the conditions that were specified above. PDE4C mRNA was found less abundant in cells and tissues used in these experiments. PDE4A was found in the lung and brain while PDE4D was confined to the lung and airway cells (A549 and NCI—H292). Since PDE7A was present in all the cells tested and has recently been suggested to be important in diseases mediated by lymphocytes, we also assessed the sub-isotypes of PDE7A. As can be seen in FIG. 2, PDE7A1 appears to be the isotype that is the most expressed in all the cells that were tested.

The PCRs were repeated several times and the presence or absence of expression of an isotype of the PDE enzymes in each cell line, primary cells or tissues is presented in Table 3a and b. It should be noted that PDE3A was not found in the PBMC and several cell lines except A549. Moreover, messengers corresponding to PDE7B and PDE4C were rarely detected in cells and tissues used here.

Example 2

This example relates to effective antisense oligonucleotides against PDE7A. Several antisense oligonucleotides against PDE7A mRNA were designed and assessed for their efficacy in the cells that express PDE7A. Table 1a includes a list of the sequences that were used. All the experiments were performed with increasing concentrations of the oligonucleotides and efficacy was assessed by comparing the ratio of PDE7A mRNA density over GAPDH density in the treated cells to that of the untreated cells.

It is to be noted in FIG. 3 that Top-1702 (SEQ. ID NO.: 1), Top-1706 (SEQ. ID NO.: 3), Top-1703 (SEQ. ID NO.: 2), Top-1701, and Top-1707, were found effective at inhibiting PDE7A mRNA expression in Eol-1 cells. In addition Top-1702 (SEQ. ID NO.: 1), Top-1703 (SEQ. ID NO.: 2), Top-1706 (SEQ. ID NO.: 3), and Top-1707, inhibited PDE7A mRNA in U937 cells. In FIG. 4, several PDE7A antisense oligonucleotides displayed more than 60% inhibition of PDE7A mRNA in Jurkat cells (Top-1702 (SEQ. ID NO.: 1), Top-1703 (SEQ. ID NO.: 2), and Top-1706 (SEQ. ID NO.: 3)) at concentrations of 10 to 20 micromolar. The oligonucleotides Top-1707 and Top-1726, were practically ineffective under the conditions studied. In Hut-78 cells the oligonucleotide Top-1703 (SEQ. ID NO.: 2) retained its efficacy at a concentration of 10 micromolar while Top-1706 (SEQ. ID NO.: 3) was less effective and Top-1702 (SEQ. ID NO.: 1) was not as effective. In BSMC and A549 cells, Top-1702 (SEQ. ID NO.: 1), Top-1703 (SEQ. ID NO.: 2) and Top-1706 (BSMC only shown, SEQ. ID NO.: 3) were all effective at downregulating mRNA expression of PDE7A as shown in FIG. 5. Moreover, these PDE7A antisenses were assessed in human PBMC. The results showed that among antisenses, Top-1706 (SEQ. ID NO.: 3) was effective at inhibiting it's specific messenger at 40%, Table 4a. The results reported here were target and antisense oligonucleotide primary sequence specific and were not due to an indirect or non-specific effect.

The overall results suggest that the antisense strategy towards PDE7A of the present invention is successful in providing significant inhibition of targeted mRNA. Among the designed oligos, Top-1703 (SEQ. ID NO.: 2), Top-1706 (SEQ. ID NO.: 3), and Top-1702 (SEQ. ID NO.: 1), seem the most effective at inhibiting mRNA expression for PDE7A in all the cell lines and primary cells studied. These results suggest that these antisense oligonucleotides could be used in the therapeutic based strategy of the present invention.

Example 3

This example relates to effective antisense oligonucleotides against PDE3A and PDE3B. A set of antisense oligonucleotides were designed and tested for their ability to decrease mRNA in several cell types. Table 1b-c includes a list of the sequences that were used.

Several antisense oligonucleotides were found to be effective at reducing PDE3A mRNA level in A549 cells and/or in U937 cells including Top-1301 (SEQ. ID NO.: 10), Top-1302 (SEQ. ID NO.: 11), Top-1303 (SEQ. ID NO.: 12), Top-1307 (SEQ. ID NO.: 13), Top-1308 (SEQ. ID NO.: 14), TOP 1309 (SEQ. ID NO.: 15), Top-1311 (SEQ. ID NO.: 16) and Top-1312 (although less effective) as shown in FIG. 6, Table 4a (above) and 4b (below). In primary bronchial smooth muscle cells the same antisense oligonucleotides were also effective at decreasing PDE3A mRNA expression as shown in FIG. 7.

Experiments performed with PBMC using the PDE3B showed that several antisenses were effective at blocking specifically the PDE3B mRNA, among these antisenses Top-1357 (SEQ. ID NO.: 18) showed 75% inhibition while Top-1351 showed 4%, as illustrated in Table 4a Taken together these results suggest that the antisense strategy of the present invention towards PDE3A and/or PDE3B inhibition is effective. Several other antisense oligonucleotides, Top-1304, Top-1305, Top-1313, Top-1351 did not provide significant mRNA inhibition, suggesting that the antisense blocking efficiency reported here was target and antisense oligonucleotide primary sequence specific but was not due to an indirect antisense effect.

Example 4

This example relates to effective antisense oligonucleotides against PDE4. Several antisense oligonucleotides against PDE4 mRNA were designed and assessed for their efficacy in the cells that express PDE4. Table 1d-f include a list of the sequences that were employed. All the experiments were performed with increasing concentrations of the oligonucleotides and efficacy was assessed by real time PCR comparing the ratio of PDE4A, -B, -D, mRNA density over HPRT (HYPOXANTHINE PHOSPHORIBOSYLTRANSFERASE, as an internal control) density in the treated cells to that of the untreated cells (Table 2c and d).

Several antisense oligonucleotides were found to be effective at reducing PDE4 mRNA level in PBMC including Top-1411 (PDE4A, SEQ. ID NO.: 21), Top-1437 (PDE4B, SEQ. ID NO.: 28) and Top-1498 (PDE4D, SEQ. ID NO.: 36), at 43, 53 and 56%, respectively, Table 4a.

Taken together these results suggest that the antisense strategy of the present invention towards PDE4 inhibition is effective. Several other antisense oligonucleotides, Top-1406 (PDE4A), Top-1430 (PDE4B), Top-1495 (PDE4D), did not provide significant mRNA inhibition, suggesting that the antisense blocking efficiency reported here was target and antisense oligonucleotide primary sequence specific but was not due to an indirect antisense effect.

Example 5

This example relates to the effect of inhibition of a single isotype of PDE on mRNA production of a different PDE. The experiments were conducted in A549 cells and in PBMC. As shown in Table 4b, several antisenses were found not only to inhibit their specific targets but were able to down regulate mRNA corresponding to other PDEs. PDE3A antisense Top-1308 (SEQ. ID NO.: 14) not only provided inhibition of it's specific mRNA in A549 cell line (60%), but also downregulated the expression of PDE3B (53%), PDE4A (63%), PDE4D (26%) and PDE7A (44%). The same experiments were done in PBMC and the results showed that, PDE3B antisense Top-1357 (SEQ. ID NO.: 18) has the capacity to inhibit specifically it's target (62%) and was also able to down regulate the messengers corresponding to PDE4A, -4B, -4D and 7A by 76, 43, 65 and 38% respectively, Table 4b. This multiple gene knock down process was also found with antisenses directed against PDE4A Top-1413 (SEQ. ID NO.: 23), against PDE4B Top-1437 (SEQ. ID NO.: 28), against PDE4D Top-1490 (SEQ. ID NO.: 34), against PDE7A Top-1706 (SEQ. ID NO.: 3) were used in PBMC, Table 4b. The observed inhibition was specific for the following reasons: All Top-antisense oligonucleotides employed in this study did not have any homology with the other PDEs nucleotide sequences studied. In addition, the effective antisenses used here did not affect all the PDEs studied, for example Top-1308 (SEQ. ID NO.: 14) which was potent against PDE3B, -4A and 7A was at lesser extent effective against -4D but had no effect on PDE4B. Moreover, several other antisenses used in this study were neither found active against their specific target nor against the other PDEs, (Top-1312, Top-1404), Table 4b. These results show that inhibition of a PDE isotype mRNA with antisense oligonucleotides affects the production of other PDEs and accounts for the single oligonucleotide induced multiple gene knock down process as described herein.

Example 6

This example relates to the effect of inhibition of a single isotype of PDE on cytokine and enzyme mRNA production. Cytokines and chemokines are mediators that are important in cell activation and recruitment. Amongst the mediators that have been shown to be increased and/or play a role in the pathophysiology of inflammatory respiratory diseases are interleukin (IL)-6, IL-7, IL-8, IL-15 and TNF-alpha. Several enzymes are directly or indirectly involved in tissue destruction and/or repair. Amongst these enzymes are matrix metalloproteinases, MMPs (MMP-1, -2, -3, -12), a tissue specific inhibitor of MMPs 1 (TIMP-1) and cyclooxygenase cox-1. It has been shown in several inflammatory respiratory diseases that there is an increase in the ratio of MMPs to their inhibitors or TIMPs. The effects of inhibition of PDE3A or of PDE7A mRNA on mediator and enzyme mRNA production by human primary smooth muscle bronchial cells was assessed.

As shown in FIG. 8, the antisense oligonucleotides that were effective at decreasing PDE3A (Top-1301 (SEQ. ID NO.: 10), Top-1303 (SEQ. ID NO.: 12), Top-1308 (SEQ. ID NO.: 14), Top-1311 (SEQ. ID NO.: 16)) or PDE7A (Top-1702 (SEQ. ID NO.: 1), Top-1703 (SEQ. ID NO.: 2), Top-1706 (SEQ. ID NO.: 3) mRNA production also decreased mRNA for IL-6, IL-7, IL-15, TNF-alpha and to a lesser degree mRNA for IL-8. The antisense oligonucleotides also had an inhibitory effect on mRNA for MMP12 but, at this concentration, there were no effects on MMP-1, MMP-2, MMP-3, TIMP-1 and cox-1 mRNA.

The effect of single PDE specific antisenses on other PDEs is given in Table 4b. Several specific PDE antisenses ((Top-1308 (SEQ. ID NO.: 14); Top-1357 (SEQ. ID NO.: 18); Top-1413 (SEQ. ID NO.: 23); Top-1437 (SEQ. ID NO.: 28); Top-1490 (SEQ. ID NO.: 34); Top-1706 (SEQ. ID NO.: 3)) not only have efficacy in down regulating their specific targets but have also inhibitory effects on other phosphodiesterases.

Here again, the observed inhibition was specific since all Top-antisense oligonucleotides employed in this study did not have any similarity with the cytokine or enzyme nucleotide sequences studied. In addition the level of Top-antisense decrease in mRNA production was sequence and cytokine specific. These results show that inhibition of a PDE isotype mRNA with antisense oligonucleotides affects mediator and enzyme production.

Example 7

This example relates to the effect of combination of isotype specific antisense oligonucleotides on PDE3A and PDE7A gene expression. The effects of combining oligonucleotides on PDE3A and PDE7A mRNA expression in U937 cells that express both isotypes of PDEs was assessed. For this, each oligonucleotide was employed separately at a concentration that was practically ineffective in this cell line under the conditions studied (10 µmolar, as shown in FIG. 9). Certain combinations of PDE3A and PDE7A antisense oligonucleotides were significantly much more effective at decreasing both PDE3A and PDE7A mRNA expression than either antisense oligonucleotide alone. The combination of Top-1703 (SEQ. ID NO.: 2) and Top-1301 (SEQ. ID NO.: 10) or Top-1706 (SEQ. ID NO.: 3) and Top-1303 (SEQ. ID NO.: 12) exhibited a strong synergistic inhibition of both PDE3A and PDE7A mRNA. In addition, the effects reported here are target and antisense primary sequence specific, since several other TOP-1700 and TOP-1300 oligonucleotide combinations did not have a significant mRNA inhibitory effect.

The effective PDE oligonucleotide antisense compounds for use in the present combinations are described herein as those capable of inhibiting expression of a target PDE gene, which when combined with another oligonucleotide compound, both at a concentration that provides less than 20% inhibition of their target PDE gene, causes at least one of the target PDE genes to be inhibited by more than 20% and at least double the amount of inhibition that is exhibited by one oligonucleotide compound alone. The combination may exhibit inhibition of both PDE nucleic acid targets as well as nucleic acid encoding other PDEs and inflammatory mediators.

These results show a specific, multiple gene knock-down effect of combining two antisense oligonucleotides derived from the nucleotide sequences of two different target genes, such as PDE7A and PDE3A. Although the oligonucleotides were administered at concentrations that had no effect on their target genes when employed alone, the combinations induced significant inhibition on the target genes.

Example 8

This example relates to the effect of the combination of PDE3A and PDE7A antisense oligonucleotides on mediator and enzyme mRNA expression. An example of the effects of multiple gene knock-down on the expression of mRNA for cytokine, chemokine and enzymatic genes is illustrated in FIG. 10. Results were obtained in the U937 monocytic cell line. It is to be noted that at the concentration studied each antisense oligonucleotide alone has a small inhibitory effect on IL-10 and MMP-8 mRNA expression. The antisense oligonucleotides when employed alone have no inhibitory effect on PDE4B, MMP-1, MMP-2 and TIMP-1 mRNA expression. The combination of 2 antisense oligonucleotides (Top-1311 (SEQ. ID NO.: 16)+Top-1703 (SEQ. ID NO.: 2) or Top-1307 (SEQ. ID NO.: 13)+Top-1703 (SEQ. ID NO.: 2)) has the same effect as each antisense oligonucleotide employed alone (mild inhibitory effects on IL-10 and MMP-8 mRNA with no effects on PDE4B, MMP-1, MMP-2 and TIMP-1 mRNA expression. However, the combination of 2 antisense oligonucleotides (Top-1301 (SEQ. ID NO.: 10)++Top-1703 (SEQ. ID NO.: 2) or Top-1303 (SEQ. ID NO.: 12)+Top-1706 (SEQ. ID NO.: 3) had a synergistic inhibitory effect as shown by the significant decrease in not only IL-10 and MMP-8 mRNA expression but also PDE4B, MMP-1 and MMP-2 mRNA expression without affecting TIMP-1 mRNA expression. The multiple gene knock down that is found by employing the last 2 combinations of antisense oligonucleotides is selective since TIMP-1, a gene that inhibits the enzymatic activity of several MMPs was unaffected and is specific since the housekeeping gene GAPDH was not affected by the combination. These results are in concurrence with those presented in example 5 and show the potential for the multiple gene knock down to have a broader anti-inflammatory effect.

Example 9

This example employs a functional assay (ie inhibition of TNF-alpha production) to illustrate the multiple gene knock down effect of combining 2 selected oligonucleotides against PDE isotypes in human PBMC.

Cytokines play a critical role in the orchestration of chronic inflammation in all diseases, including asthma and COPD. TNF-alpha is one of the most important pro-inflammatory cytokines that is expressed in several inflammatory diseases. TNF-alpha levels are markedly increased in induced sputum of patients with COPD (Keatings et al., Am. J. Respir. Crit.

Care Med. 1996; 153; 530-534.). Furthermore, there is evidence that COPD patients with weight loss show increased release of TNF-alpha from circulating cells and that TNF-alpha may induce apoptosis of skeletal muscle cells, resulting in the characteristic muscle wasting and cachexia seen in some patients with severe COPD (De Godoy et al., Am. J. Respir. Crit. Care Med. 1996, 153, 633-637.).

PDE4 inhibitors caused a decrease in the release of cytokines and chemokines from inflammatory cells via an increase in intracellular cyclic AMP (Torphy, Am. J. Respir. Crit. Care Med. 1998, 157, 351-370). In contrast to corticosteroids, PDE4 inhibitors have a potent inhibitory effect on neutrophils (Au et al., Br. J. Pharmacol. 1998, 123, 1260-1266.) indicating that they may be useful anti-inflammatory treatments for COPD. There is preliminary evidence that a PDE4 inhibitor Cilomilast improves lung function and symptoms in patients with COPD and this may be due to cytokine inhibition (Compton et al., Lancet. 2001, 358, 265-270). Here it is shown that a combination of several selected antisense oligonucleotides, not only inhibited their specific PDE targets but also caused multiple gene knock-down, including a decrease in the production of the pro-inflammatory cytokine TNF-alpha FIG. 11 shows that when antisense oligonucleotides (Top-1360 (PDE3B, SEQ. ID NO.: 19); Top-1413 (PDE4A, SEQ. ID NO.: 23); Top-1437 (PDE4B, SEQ. ID NO.: 28); Top-1498 (PDE4D, SEQ. ID NO.: 36)) were used individually they have a small, minimal effect on TNF-alpha release from PHA-activated PBMC at the concentration tested. However, when combinations were assessed, they provide a more than additive effect on TNF-alpha release from PBMC. The observed effect on TNF-alpha release was specific since the use of mismatch antisenses individually or in combination with other antisenses had no effect on TNF-alpha release from stimulated PBMC.

Because TNF-alpha, is considered as a common denominator in inflammatory and chronic respiratory diseases, this invention provides a broad therapeutic application for treating several inflammatory diseases.

Example 10

This example shows that it is possible to decrease expression of mRNA for PDE4A, PDE4B and PDE7A by administering an antisense oligonucleotide directed against a PDE isotype in vivo. In this experiment, each antisense oligonucleotide (Table 5) was administered by nasal instillation (50 mg) and lungs collected 16 h later. The expression of target mRNA was assessed by real-time PCR on the cDNA prepared from whole lung. Table 5 lists several antisense oligonucleotides specific to each murine target mRNA for which the inhibitory activity measured was greater than 25%. A control antisense oligonucleotide that was included in each experiment showed no inhibitory activity of the different mRNA targets suggesting that the antisense activity observed was target and antisense oligonucleotide sequence specific. Therefore, inhibition of the expression of several PDE mRNAs can be achieved in the lung of mice by simple nasal instillation of active antisense oligonucleotides.

Example 11

This example demonstrates that a combination of 2 antisense oligonucleotides can be employed to induce multiple gene knock down in vivo. FIG. 12A shows that at the time point measure TOP 2437, a murine antisense oligonucleotide directed against PDE4B has no significant inhibitory effect on PDE4B mRNA expression on its own when used at low concentration (50 mg/mouse). However, combining Top 2437 (an antisense oligonucleotide directed against PDE4B) with Top 2713 (an antisense oligonucleotide directed against PDE7A) leads to a more than 40% inhibition of PDE4B in mice lungs. FIG. 12B shows that although TOP2437 and TOP2713 alone had little inhibitory effect on PDE7A mRNA expression when used at low concentrations, the combination of both antisense oligonucleotides inhibited PDE7A mRNA expression by 83%. Results show that a combination of two antisenses targeting two different PDE isozymes resulted in higher level of inhibition of each target gene than single antisense treatment, e.g. a more than additive level of inhibition.

FIG. 12C shows that a combination of antisense oligonucleotides directed against PDE4B and PDE7A will also decrease PDE4A mRNA expression in murine lungs. Results showed that even though each antisense oligonucleotide had no effect on its own, a high synergistic level of inhibition of PDE4A mRNA expression was achieved following the combination treatment.

These results demonstrate not only that a more than additive inhibition of targeted PDE isotypes can be obtained by combining 2 antisense oligonucleotides directed against these isotypes, but that additional inhibition of other PDE isotypes can also be achieved by treatment with a combination of two antisenses that were not directed against a given isotype.

Example 12

This example shows that an antisense oligonucleotide against a specific PDE isotype can partially inhibit the acute lung inflammation induced in mice by LPS (FIG. 13). PDE4B was targeted in this example because it was previously shown to be of importance in the LPS induced inflammatory (Ma et al., Mol. Pharmacol., 1999, 55, 50-57.; Wang et al., Molec. Pharmacol., 1999, 56, 170-174.). In addition, our previous results confirmed that PDE4B expression was up-regulated by LPS treatment in mice (data not shown).

To demonstrate that expression of target mRNAs could be inhibited in LPS-exposed mice, mice were pre-treated by nasal instillation of 200 mg of TOP2430 (specific to PDE4B) or control antisense oligonucleotide 12 h prior to LPS exposure. As shown in FIG. 13A, PDE4B expression was reduced by 86% following TOP2430 pre-treatment. FIG. 13A also shows that lung PDE4A, 4D and 7A mRNA expression was also partially inhibited by employing an antisense oligonucleotide against PDE4B. In contrast, PDE3B expression was stimulated following the inhibition of PDE4B by 117%. This example demonstrates in another way the concept of multiple gene knock down in vivo.

FIG. 13B shows the effect of PDE4B inhibition on the LPS-induced acute lung inflammation. Results show that inhibition of PDE4B by TOP2430 significantly reduced the cellular influx (40% reduction, $p<0.013$) in the lungs of mice exposed to LPS when compared to control mice. In treated mice, the reduction of total cells was associated with a significant decrease in neutrophils (40% reduction, $p<0.016$) and in macrophages (50% reduction, $p<0.002$) that were present in the lung lavage. Moreover, pre-treatment with TOP2430 caused a significant decrease (26%) in LPS-induced TNF-alpha concentration in lung lavage fluid (FIG. 13C).

Results show that specific inhibition of target PDE mRNA can be achieved by topical delivery of antisense oligonucleotides in mice. Moreover, inhibition of PDE4B expression in LPS-exposed mice has a significant effect on the inflammatory response with decreased cellular influx, neutrophil and macrophage migration to the lung and a decrease in TNF-alpha release. The mechanism of this effect may be related to the multiple gene knock down that occurs when an antisense oligonucleotide directed against PDE4B results also in the down-regulation of several other PDEs.

Example 13

This example relates to the efficacy of antisense oligonucleotides targeting at specific PDEB4 mRNAs to inhibit acute lung inflammation induced by cigarette smoke exposure (FIG. 14).

FIG. 14 shows the effect of having AKR/J mice breathe in cigarette smoke. Smoke produced a significant increase in bronchoalveolar lavage cells (neutrophils and macrophages) by 24 h after exposure that persisted for at least 48 hours (FIG. 14A). In conjunction with the influx of inflammatory cells, smoke exposure induced an increased expression of TNF-alpha in the lung tissue (3.5-fold increase, FIG. 14B). It has been shown that macrophages, neutrophils and TNF-alpha play important roles in smoke-induced lung inflammation and progression to subsequent emphysema (Churg et al., Am. J. Respir. Crit. Care Med., 2002, 166, 849-854.; Am. J. Respir. Cell Mol. Biol., 2002, 27, 368-374).

FIG. 14C shows the effect of PDE4B inhibition on smoke-induced increase of TNF-alpha mRNA expression. Results showed that inhibition of PDE4B by 20% with TOP2430 reduced the expression of TNF-alpha in lung tissue by 21% when compared to mice that were pre-treated with a control antisense oligonucleotide.

Taken altogether, these results show that specific inhibition of PDE4B mRNA expression can be obtained in smoke-exposed mice and that it has a comparable effect on TNF-alpha mRNA expression in whole lung tissue.

TABLE 1a

| Antisense identification | Antisense sequence identification (5'-3') | Target gene | Accession number | Seq ID No. |
| --- | --- | --- | --- | --- |
| TOP-1702 | GAACCTCTTCTTTCTGATTC | PDE7A | NM_002603 | 1 |
| TOP-1703 | GGTGAGAACCTCTTCTTTCT | PDE7A | NM_002603 | 2 |
| TOP-1706 | TTCCCACGTCCGACATG | PDE7A | NM_002603 | 3 |
| TOP-1714 | GCTTAGGTTCCTTTAAGT | PDE7A | NM_002603 | 4 |
| TOP-1716 | TCATGAGTGGCAGCTGC | PDE7A | NM_002603 | 5 |
| TOP-1718 | CCATTTGTTGCCTGCTTTC | PDE7A | NM_002603 | 6 |
| TOP-1719 | GTCTCCATTTGTTGCCTGC | PDE7A | NM_002603 | 7 |
| TOP-1720 | TTTCACTCCACTGCTTGCT | PDE7A | NM_002603 | 8 |
| TOP-1722 | CTGTGGTAATCTTCTTGAA | PDE7A | NM_002603 | 9 |

TABLE 1b

| Antisense identification | Antisense sequence identification (5'-3') | Target gene | Accession number | Seq ID No. |
| --- | --- | --- | --- | --- |
| TOP-1301 | GACTCGTGCAGCGTCGCC | PDE3A | NM_000921 | 10 |
| TOP-1302 | GTTCCTGACTCGTGCAG | PDE3A | NM_000921 | 11 |
| TOP-1303 | GGCTTGTTCCTGACTCGTGC | PDE3A | NM_000921 | 12 |
| TOP-1307 | GCTCCGGAGCGGCTGCAGC | PDE3A | NM_000921 | 13 |
| TOP-1308 | GGCCAGCAGCGCGACAGCCAG | PDE3A | NM_000921 | 14 |
| TOP-1309 | GCGGACCAGCCTCACC | PDE3A | NM_000921 | 15 |
| TOP-1311 | CGGCCAAGCAGCTGAGCACC | PDE3A | NM_000921 | 16 |

TABLE 1c

| Antisense identification | Antisense sequence identification (5'-3') | Target gene | Accession number | Seq ID No. |
| --- | --- | --- | --- | --- |
| TOP-1353 | GGCGGCTGCAGGGACCGC | PDE3B | NM_000922 | 17 |
| TOP-1357 | CCGCAGCTCCACGTTGCAG | PDE3B | NM_000922 | 18 |
| TOP-1360 | TCAGCAGCGTCCGCAGCAG | PDE3B | NM_000922 | 19 |

TABLE 1d

| Antisense identification | Antisense sequence identification (5'-3') | Target gene | Accession number | Seq ID No. |
| --- | --- | --- | --- | --- |
| TOP-1403 | CGGAGGCTGGCCAGCACCTG | PDE4A | NM_006202 | 20 |
| TOP-1411 | TCTTGCGTAGGCTCTGC | PDE4A | NM_006202 | 21 |
| TOP-1412 | CACTTTCTTGGTCTCCACC | PDE4A | NM_006202 | 22 |
| TOP-1413 | GCCACGCTCGCGCTCTC | PDE4A | NM_006202 | 23 |
| TOP-1505 | GTCCACTGGCGGTACAG | PDE4A | NM_006202 | 24 |

TABLE 1d-continued

| Antisense identification | Antisense sequence identification (5'-3') | Target gene | Accession number | Seq ID No. |
|---|---|---|---|---|
| TOP-1510 | GTCATAGTCGCTGTCTG | PDE4A | NM_006202 | 25 |
| TOP-1512 | CCATGATGCGGTCTGTCCA | PDE4A | NM_006202 | 26 |

TABLE 1e

| Antisense identification | Antisense sequence identification (5'-3') | Target gene | Accession number | Seq ID No. |
|---|---|---|---|---|
| TOP-1432 | GACCGGTAGGTCTGTATGGT | PDE4B | NM_002600 | 27 |
| TOP-1437 | GGAGGTCTCTTTCCTGG | PDE4B | NM_002600 | 28 |
| TOP-1534 | CGGTGCTACTGAAGGTG | PDE4B2 | NM_002600 | 29 |
| TOP-1537 | CTGATTCCGGTGCTACT | PDE4B2 | NM_002600 | 30 |
| TOP-1538 | CTGATTCCGGTGCTACTG | PDE4B2 | NM_002600 | 31 |
| TOP-1539 | CTGATTCCGGTGCTACTGA | PDE4B2 | NM_002600 | 32 |

TABLE 1f

| Antisense identification | Antisense sequence identification (5'-3') | Target gene | Accession number | Seq ID No. |
|---|---|---|---|---|
| TOP-1489 | CCGGTCCGTCCACTGGCG | PDE4D | NM_006203 | 33 |
| TOP-1490 | CGTTCCCTCTCTCGGTCTCC | PDE4D | NM_006203 | 34 |
| TOP-1497 | CTGCCTCCTCTTCAACCTG | PDE4D | NM_006203 | 35 |
| TOP-1498 | CTTCAGGCTGGCTTTCCTC | PDE4D | NM_006203 | 36 |

TABLE 2a

| PDE ISOFORM | SENSE PRIMER (5'-3') | ANTISENSE PRIMER (5'-3') | PRODUCT SIZE (bp) | SEQ ID NOS |
|---|---|---|---|---|
| PDE3A | CCTATTCCAGGCCTCTCAAC | GCCAACCGTTGCTCCTCTTC | 940 | 37/38 |
| PDE3B | GGAAGGATTCTCAGTCAGG | CAGTGAGGTGGTGCATTAG | 1085 | 39/40 |
| PDE7A | CCTTACCATAACGCAGTCC | GAGCACCTATCTGTGTCTC | 284 | 41/42 |
| PDE7A1 | CCAGCCTCTGCTGCCTCTGGC | GCTTACCTACCAACCTTCC | 665 | 43/44 |
| PDE7A2 | CTGGTGTCTGGCCTTGGTTC | GCATACACTTGGCTTGTTC | 348 | 45/46 |
| PDE7A3 | CGAAGACCAGCTTCTGCCAC | GGCCTCGTGCTTCTGGTGTGG | 379 | 47/48 |
| PDE7B | CCACCTCGCACACAACAAGG | GCAGCGAATGCTGAGGTGAC | 305 | 49/50 |
| PDE4A | CAACGATGAGTCGGTGCTCG | CACTGCCTCCAGCTCGGCCTCC | 802 | 51/52 |
| PDE4B | CTGCACGCTGCTGATGTAGC | CCTGAGCATCAGGCTGTACC | 654 | 53/54 |
| PDE4C | GACGCCTCGGTGCTGGAGAAC | GATCTTGCTCTGGTACCAC | 518 | 55/56 |
| PDE4D | GACATCGTACTTGCAACAG | GTACCATTCACGATTGTCC | 385 | 57/58 |

TABLE 2b

| | SENSE PRIMER (5'-3') | ANTISENSE PRIMER (5'-3') | PRODUCT SIZE (bp) | SEQ ID NOS |
|---|---|---|---|---|
| IL-6[a] | CTTTTGGAGTTTGAGGTATACCTA | GCTGCGCAGAATGAGATGAGTTGTC | 236 | 59/60 |
| IL-7[b] | TTTTATTCCGTGCTGCTCGC | GCCCTAATCCGTTTTGACCA | 429 | 61/62 |
| IL-8[a] | ACATACTCCAAACCTTTCCAC | TCTTCAAAAACTTCTCCACAAC | 168 | 63/64 |
| IL-10[b] | AAAAGAAGGCATGCACAGCTC | CAATAAGGTTTCTCAAGGGGCTGG | 653 | 65/66 |
| IL-15[b] | TGTCTTCATTTTGGGCTGTTTCA | TCCTCCAGTTCCTCACATTCTTTG | 327 | 67/68 |
| TNFalpha[a] | AACGGAGGCTGAACAATAGGC | AGCAACCTTTATTTCTCGCCAC | 206 | 69/70 |
| MMP-1[c] | CGACTCTAGAAACACAAGAGCAAGA | AAGGTTAGCTTACTGTCACACGCTT | 786 | 71/72 |
| MMP-2[c] | GTGCTGAAGGACACACTAAAGAAGA | TTGCCATCCTTCTCAAAGTTGTAGG | 580 | 73/74 |
| MMP-3[c] | AGATGCTGTTGATTCTGCTGTTGAG | ACAGCATCAAAGGACAAAGCAGGAT | 515 | 75/76 |
| MMP-8[c] | GCTGCTTATGAAGATTTTGACAGAG | ACAGCCACATTTGATTTTGCTTCAG | 435 | 77/78 |
| MMP-12 | CCTTGCCATCTGGCATTGAAG | GGTGATACGTTGGAGTAGGAAGTC | 397 | 79/80 |
| TIMP-1[d] | GGCCTTAGGGGATGCCG | CGGCTATCTGGGACCGCA | 403 | 81/82 |

TABLE 2b-continued

| | SENSE PRIMER (5'-3') | ANTISENSE PRIMER (5'-3') | PRODUCT SIZE (bp) | SEQ ID NOS |
|---|---|---|---|---|
| Cox-1[d] | TGCCCAGCTCCTGGCCCGCCGCTT | GTGCATCAACACAGGCGCCTCTTC | 303 | 83/84 |
| PBGD | TGCAACGGCGGAAGAAAAC | GGCTCCGATGGTGAAGCC | 313 | 85/86 |
| GAPDH | GGTAAAGTGGATATTGTTGC | CAGTCTTCTGGGTGGCAGTG | 448 | 87/88 |

[a]Gaede, K. I. Et al. (1999) J. Mol. Med. 77, 847-852
[b]Kebelmann-Betzing, C. et al. (2001) Cytokine. 13, 39-50.
[c]Ishii, Y. et al. (2003) Int. J. Cancer. 103, 161-168.

TABLE 2c

| Gene | Primer name | Primer sequence (5'-3') |
|---|---|---|
| DE3A | hu/muPDE3A F | CAACAGTGACAGCAGTGACATT (SEQ ID NO: 89) |
| | hu/muPDE3A R | TTGAGTCCAGGTTATCCATGAC (SEQ ID NO: 90) |
| PDE3B | huPDE3B F1 | GATTCTTTGGGATTGGGACT (SEQ ID NO: 91) |
| | hu/muPDE3B R1 | ATCTTTGGCCTACAGGAACC (SEQ ID NO: 92) |
| PDE4A | hu/muPDE4A F1 | ATCAACACCAATTCGGAGCT (SEQ ID NO: 93) |
| | hu/muPDE4A R1 | CCAGCACCATGTCGATGAC (SEQ ID NO: 94) |
| PDE4B | huPDE4B F1 | TGGCAGACCTGAAGACAATG (SEQ ID NO: 95) |
| | huPDE4B R2 | AAATTCCTCCATGATGCGG (SEQ ID NO: 96) |
| PDE4D | hu/muPDE4D F1 | CAGAATATGGTGCACTGTGC (SEQ ID NO: 97) |
| | hu/muPDE4D R1 | AGTCTATGAAGCCCACCTGTG (SEQ ID NO: 98) |
| PDE7A | hu/muPDE7 F2 | TCAGGCCATGCACTGTTACT (SEQ ID NO: 99) |
| | huPDE7 R2 | CCTGATTCTCTCAATAAGCCC (SEQ ID NO: 100) |
| TNF-alpha | TNFa-F | AACGGAGGCTGAACAATAGGC (SEQ ID NO: 101) |
| | TNFa-R | AGCAACCTTTATTTCTCGCCAC (SEQ ID NO: 102) |
| IL-6 | hu IL-6 F | CTTTTGGAGTTTGAGGTATACCTAG (SEQ ID NO: 103) |
| | hu IL-6 R | CGCAGAATGAGATGAGTTGTC (SEQ ID NO: 104) |
| IL-10 | hu IL-10 F | TGCTGGAGGACTTTAAGGGTTAC (SEQ ID NO: 105) |
| | hu IL-10 R | GTAGATGCCTTTCTCTTGGAGC (SEQ ID NO: 106) |
| HPRT | HPRT exon 3.4 | ATCAGACTGAAGAGCTTTGTAATGACCA (SEQ ID NO: 107) |
| | HPRT exon7 | TGGCTTATATCCAACACTTCGTG (SEQ ID NO: 108) |

TABLE 2d

| Gene | Primer name | Primer sequence (5'-3') |
|---|---|---|
| DE3B | muPDE3B F1 | ATCCTCTGGGACTGGGACTT (SEQ ID NO: 109) |
| | hu/muPDE3B R1 | ATCTTTGGCCTACAGGAACC (SEQ ID NO: 110) |
| PDE4A | muPDE4A F2 | GCGTCTCCAACCAGTTCCTA (SEQ ID NO: 111) |
| | hu/muPDE4A R1 | CCAGCACCATGTCGATGAC (SEQ ID NO: 112) |
| PDE4B | muPDE4B F1 | AAGGTGACAAGCTCCGGT (SEQ ID NO: 113) |
| | hu/muPDE4B R1 | TCTTTGTCTCCCTGCTGGA (SEQ ID NO: 114) |
| PDE4D | hu/muPDE4D F1 | CAGAATATGGTGCACTGTGC (SEQ ID NO: 115) |
| | hu/muPDE4D R1 | AGTCTATGAAGCCCACCTGTG (SEQ ID NO: 116) |
| PDE7A | hu/muPDE7 F1 | CTCAGGCCATGCACTGTTAC (SEQ ID NO: 117) |
| | muPDE7 R2 | GGCAAGTGTGAGAACAAACC (SEQ ID NO: 118) |
| TNF-alpha | muTNF-alpha F | TGCTCAGAGCTTTCAACAACTACTC (SEQ ID NO: 119) |
| | muTNF-alpha R | GAGGCTCCAGTGAATTCGGA (SEQ ID NO: 120) |
| IL-6 | mu IL-6 F | ATGGATGCTACCAAACTGGAT (SEQ ID NO: 121) |
| | mu IL-6 R | GCCACTCCTTCTGTGACTCC (SEQ ID NO: 122) |
| PBGD | mPBGD F | TTGTACCCTGGCATACAGTTTGA (SEQ ID NO: 123) |
| | mPBGD R | GTTCCCACGGCACTTTC (SEQ ID NO: 124) |

HU: HUMAN
HPRT: HYPOXANTHINE PHOSPHORIBOSYLTRANSFERASE
MU: MOUSE
PBGD: PORPHOBILINOGEN DEAMINASE

TABLE 3a

| PDE | Cell lines | | | | | | | |
|---|---|---|---|---|---|---|---|---|
| Isotype | A549 | U937 | EOL-1 | Jurkat | Hut-78 | HL-60 | Daudi | NCI-H292 |
| PDE3A | ++ | − | − | − | − | − | − | − |
| PDE3B | ++ | ++ | ++ | ++ | ++ | ++ | − | ++ |
| PDE7A | ++ | ++ | ++ | ++ | ++ | + | + | ++ |
| PDE7B | − | − | − | − | +/− | − | − | − |
| PDE4A | +/− | + | +++ | +++ | +++ | ++ | + | + |

TABLE 3a-continued

| PDE Isotype | Cell lines | | | | | | | |
|---|---|---|---|---|---|---|---|---|
| | A549 | U937 | EOL-1 | Jurkat | Hut-78 | HL-60 | Daudi | NCI-H292 |
| PDE4B | +++ | ++ | ++ | − | +++ | − | + | ++ |
| PDE4C | − | − | − | − | + | − | − | − |
| PDE4D | ++ | − | + | − | ++ | − | − | + |

TABLE 3b

| PDE Isotype | Primary cells | | | Tissue | |
|---|---|---|---|---|---|
| | NHBE | BSMC | Macro. | Lung | Brain |
| PDE3A | − | + | − | + | ++ |
| PDE3B | − | ++ | − | +++ | ++ |
| PDE7A | + | + | + | ++ | ++ |
| PDE7B | +/− | − | − | − | − |
| PDE4A | ++ | − | ++ | ++ | ++ |
| PDE4B | +/− | ++ | + | +++ | +++ |
| PDE4C | +/− | − | − | +/− | +/− |
| PDE4D | + | + | + | ++ | + |

TABLE 4a

Human PDE antisenses primary screening

| PDE Isoform | Cell Type | Antisense Dose | Antisense ID | % of mRNA Inhibition |
|---|---|---|---|---|
| PDE3A | A549 | 1 ug | TOP1312 | 6% |
| | | | TOP1308 | 54% |
| PDE4A | PBMC | 2 uM | TOP1406 | −15% |
| | | | TOP1411 | 43% |
| PDE4B | PBMC | 5 uM | TOP1432 | 14% |
| | | | TOP1437 | 53% |
| PDE4D | PBMC | 2 uM | TOP1495 | 3% |
| | | | TOP1498 | 56% |
| PDE7A | PBMC | 5 uM | TOP1711 | 5% |
| | | | TOP1706 | 40% |
| PDE3B | PBMC | 0.1 uM | TOP1351 | 4% |
| | | | TOP1357 | 75% |

TABLE 4b

Human PDE single antisenses with multiple gene knock down effects

| Targeted PDE Isoform | Antisense ID | Antisense Dose | Cell Type | % of PDE mRNA Inhibition | | | | | |
|---|---|---|---|---|---|---|---|---|---|
| | | | | 3A | 3B | 4A | 4B | 4D | 7A |
| PDE3A | TOP1312 | 1 ug | A549 | 12% | 16% | 18% | — | 16% | 6% |
| | TOP1308 | | | 60% | 53% | 63% | −55 | 26% | 44% |
| PDE3B | TOP1352 | 0.05 uM | PBMCs | — | −51% | — | — | — | — |
| | TOP1357 | | | | 43% | 73% | 24% | 28% | 38% |
| PDE4A | TOP1404 | 2 uM | PBMCs | — | −30% | 1% | −10% | −4% | −18% |
| | TOP1413 | | | | 56% | 76% | 82% | 63% | 25% |
| PDE4B | TOP1432 | 5 uM | PBMCs | — | −7% | 5% | 15% | 15% | −14% |
| | TOP1437 | | | | 42% | 33% | 60% | 53% | 27% |
| PDE4D | TOP1494 | 2 uM | PBMCs | — | 12% | 13% | 26% | 15% | 12% |
| | TOP1490 | | | | 77% | 94% | 79% | 78% | 64% |
| PDE7A | TOP1711 | 5 uM | PBMCs | — | 7% | — | — | −7% | 5% |
| | TOP1706 | | | | 38% | 70% | 49% | 58% | 40% |

TABLE 5

Mouse PDE antisenses in vivo primary screening

| Antisense Identification | Target Gene | Antisense Sequence (5'-3') | Target Sequence | Accession Number | SEQ ID NOS |
|---|---|---|---|---|---|
| TOP2406 | PDE4A | TGTGCTAAGAGGTCCTC | GAGGACCTCTTAGCACA | BC027224 | 125/126 |
| TOP2410 | PDE4A | AGACTCATCGTTGTACAT | ATGTACAACGATGAGTCT | BC027224 | 127/128 |
| TOP2411 | PDE4A | ACCATGTCGATGACCATCTT | AAGATGGTCATCGACATGGT | BC027224 | 129/130 |
| TOP2412 | PDE4A | ACCATAGTCTTCAGGTCAG | CTGACCTGAAGACTATGGT | BC027224 | 131/132 |
| TOP2426 | PDE4B | CTAGTTCCTCCAGCGTCTCC | GGAGACGCTGGAGGAACTAG | BC023751 | 133/134 |
| TOP2430 | PDE4B | CATCTCTGAGAGGTGTGTC | GACACACCTCTCAGAGATG | BC023751 | 135/136 |
| TOP2433 | PDE4B | GACAGAGCGGTAGGTCTG | CAGACCTACCGCTCTGTC | BC023751 | 137/138 |
| TOP2435 | PDE4B | CTGATTGGAGACTCCAGG | CCTGGAGTCTCCAATCAG | BC023751 | 139/140 |
| TOP2437 | PDE4B | GATGGACAATGTAGTCAAT | ATTGACTACATTGTCCATC | BC023751 | 141/142 |
| TOP2707 | PDE7A | TCCAGATCGTGAGTGGC | GCCACTCACGATCTGGA | BC062909 | 143/144 |
| TOP2711 | PDE7A | CTTGCTTAATTCCCAGTTC | GAACTGGGAATTAAGCAAG | BC062909 | 145/146 |
| TOP2712 | PDE7A | GTCAGAACCAGTTCTTC | GAAGAACTGGTTCTGAC | BC062909 | 147/148 |
| TOP2713 | PDE7A | GGAGCAATCTTACAGCTTC | GAAGCTGTAAGATTGCTCC | BC062909 | 149/150 |

We claim:

1. A pharmaceutical composition for treating disease associated with reduced cAMP levels, said composition comprising a pharmaceutically acceptable carrier and at least two antisense oligonucleotide compounds each being capable of inhibiting expression of a target PDE consisting of PDE7A and PDE4B respectively, each oligonucleotide being directed against at least a portion of a nucleic acid sequence encoding PDE7A and PDE4B respectively, each oligonucleotide compound being present at a concentration that exhibits 20% inhibition of expression of its target PDE, the combination exhibiting more than 20% inhibition of expression, and at least doubling the inhibition of expression of at least one target PDE resulting in a more than additive inhibition of expression of PDE7A and PDE4B.

2. A composition as defined in claim 1, wherein the combination exhibits inhibition of more than one target PDE.

3. A composition as defined in claim 1, wherein the combination exhibits inhibition of other PDE isotypes.

4. A pharmaceutical composition according to claim 1, comprising an oligonucleotide compound directed against a nucleic acid coding for PDE7A consisting of Seq. ID No. 5 and an oligonucleotide compound directed against a nucleic acid coding for PDE4B selected from the group consisting Seq. ID No. 28.

5. A formulation, comprising the composition of claim 1, being a topical formulation.

6. A formulation comprising the composition of claim 1, being an intrapulmonary formulation.

7. The formulation of claim 6, wherein the carrier is selected from the group consisting of solid and liquid carriers.

8. An article of manufacture comprising packaging material contained within which is an antisense oligonucleotide composition that is therapeutically effective to treat a disease associated with reduced cAMP in a subject, said composition comprising a pharmaceutically acceptable carrier and an antisense oligonucleotide compound that is effective to inhibit a PDE gene, said oligonucleotide compound being at least 50% complementary to the gene, said packaging material comprising a label which indicates that the composition is useful to treat said disease.

9. An article of manufacture comprising packaging material contained within which is the composition of claim 1 that is therapeutically effective to a disease associated with reduced cAMP in a subject, the packaging material of the article comprising a label indicating that the composition can be used to treat said disease.

10. An article of manufacture as defined in claim 9, wherein said label indicates that the composition is used to treat PDE-related disease.

11. The composition as defined in claim 1, wherein at least a portion of the oligonucleotides hybridizes with RNA to form an oligonucleotide-RNA duplex.

12. The composition as defined in claim 1, wherein the antisense oligonucleotide compound directed against PDE4B additionally inhibit expression of PDE4D.

* * * * *

SEQUENCE LISTING

<160> NUMBER OF SEQ ID NOS: 150

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
gaacctcttc tttctgattc                                            20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
ggtgagaacc tcttctttct                                            20

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
ttcccacgtc cgacatg                                               17

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
gcttaggttc ctttaagt                                              18

```
<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tcatgagtgg cagctgc                                                  17

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccatttgttg cctgctttc                                                19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtctccattt gttgcctgc                                                19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tttcactcca ctgcttgct                                                19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctgtggtaat cttcttgaa                                                19

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gactcgtgca gcgtcgcc                                                 18
```

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gttcctgact cgtgcag                                               17

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggcttgttcc tgactcgtgc                                            20

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gctccggagc ggctgcagc                                             19

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggccagcagc gcgacagcca g                                          21

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcggaccagc ctcacc                                                16

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cggccaagca gctgagcacc                                            20

```
<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggcggctgca gggaccgc                                                   18

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccgcagctcc acgttgcag                                                  19

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tcagcagcgt ccgcagccag                                                 20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cggaggctgg ccagcacctg                                                 20

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tcttgcgtag gctctgc                                                    17

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cactttcttg gtctccacc                                                  19

<210> SEQ ID NO 23
```

```
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gccacgctcg cgctctc                                                17

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gtccactggc ggtacag                                                17

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gtcatagtcg ctgtctg                                                17

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ccatgatgcg gtctgtcca                                              19

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gaccggtagg tctgtatggt                                             20

<210> SEQ ID NO 28
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ggaggtctct ttcctgg                                                17

<210> SEQ ID NO 29
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cggtgctact gaaggtg                                                   17

<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ctgattccgg tgctact                                                   17

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ctgattccgg tgctactg                                                  18

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ctgattccgg tgctactga                                                 19

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ccggtccgtc cactggcg                                                  18

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cgttccctct ctcggtctcc                                                20

<210> SEQ ID NO 35
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 35
ctgcctcctc ttcaacctg                                               19

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cttcaggctg gctttcctc                                               19

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cctattccag gcctctcaac                                              20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gccaaccgtt gctcctcttc                                              20

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ggaaggattc tcagtcagg                                               19

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cagtgaggtg gtgcattag                                               19

<210> SEQ ID NO 41
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 41
ccttaccata acgcagtcc                                                    19

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gagcacctat ctgtgtctc                                                    19

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ccagcctctg ctgcctctgg c                                                 21

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gcttacctac caaccttcc                                                    19

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ctggtgtctg gccttggttc                                                   20

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gcatacactt ggcttgtcc                                                    19

<210> SEQ ID NO 47
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 47
cgaagaccag cttctgccac                                                    20

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ggcctcgtgc ttctggtgtg g                                                  21

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ccacctcgca cacaacaagg                                                    20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gcagcgaatg ctgaggtgac                                                    20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
caacgatgag tcggtgctcg                                                    20

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cactgcctcc agctcggcct cc                                                 22

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 53
ctgcacgctg ctgatgtagc                                               20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
cctgagcatc aggctgtacc                                               20

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gacgcctcgg tgctggagaa c                                             21

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gatcttgctc tggtaccac                                                19

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gacatcgtac ttgcaacag                                                19

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gtaccattca cgattgtcc                                                19

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cttttggagt tgaggtata ccta                                    24

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gctgcgcaga atgagatgag ttgtc                                  25

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ttttattccg tgctgctcgc                                        20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gccctaatcc gttttgacca                                        20

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
acatactcca aacctttcca c                                      21

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
tcttcaaaaa cttctccaca ac                                     22

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 65
aaaagaaggc atgcacagct c                                              21

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
caataaggtt tctcaagggg ctgg                                           24

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
tgtcttcatt ttgggctgtt tca                                            23

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
tcctccagtt cctcacattc tttg                                           24

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
aacggaggct gaacaatagg c                                              21

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
agcaaccttt atttctcgcc ac                                             22

<210> SEQ ID NO 71
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
```

```
cgactctaga aacacaagag caaga                                               25

<210> SEQ ID NO 72
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
aaggttagct tactgtcaca cgctt                                               25

<210> SEQ ID NO 73
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gtgctgaagg acacactaaa gaaga                                               25

<210> SEQ ID NO 74
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ttgccatcct tctcaaagtt gtagg                                               25

<210> SEQ ID NO 75
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
agatgctgtt gattctgctg ttgag                                               25

<210> SEQ ID NO 76
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
acagcatcaa aggacaaagc aggat                                               25

<210> SEQ ID NO 77
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
```
gctgcttatg aagattttga cagag        25

<210> SEQ ID NO 78
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
acagccacat tgatttttgc ttcag        25

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ccttgccatc tggcattgaa g        21

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ggtgatacgt tggagtagga agtc        24

<210> SEQ ID NO 81
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ggccttaggg gatgccg        17

<210> SEQ ID NO 82
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
cggctatctg ggaccgca        18

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
tgcccagctc ctggcccgcc gctt        24

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gtgcatcaac acaggcgcct cttc                                          24

<210> SEQ ID NO 85
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
tgcaacggcg gaagaaaac                                                19

<210> SEQ ID NO 86
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
ggctccgatg gtgaagcc                                                 18

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ggtaaagtgg atattgttgc                                               20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
cagtcttctg ggtggcagtg                                               20

<210> SEQ ID NO 89
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
caacagtgac agcagtgaca tt                                            22

```
<210> SEQ ID NO 90
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ttgagtccag gttatccatg ac                                              22

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gattctttgg gattgggact                                                 20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
atctttggcc tacaggaacc                                                 20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
atcaacacca attcggagct                                                 20

<210> SEQ ID NO 94
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
ccagcaccat gtcgatgac                                                  19

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
tggcagacct gaagacaatg                                                 20
```

```
<210> SEQ ID NO 96
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
aaattcctcc atgatgcgg                                                19

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
cagaatatgg tgcactgtgc                                               20

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
agtctatgaa gcccacctgt g                                             21

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
tcaggccatg cactgttact                                               20

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
cctgattctc tcaataagcc c                                             21

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
aacggaggct gaacaatagg c                                             21

<210> SEQ ID NO 102
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
agcaaccttt atttctcgcc ac                                              22

<210> SEQ ID NO 103
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
cttttggagt ttgaggtata cctag                                           25

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
cgcagaatga gatgagttgt c                                               21

<210> SEQ ID NO 105
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
tgctggagga ctttaagggt tac                                             23

<210> SEQ ID NO 106
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
gtagatgcct ttctcttgga gc                                              22

<210> SEQ ID NO 107
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
atcagactga agagctttgt aatgacca                                        28

<210> SEQ ID NO 108
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
tggcttatat ccaacacttc gtg                                           23

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
atcctctggg actgggactt                                               20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
atctttggcc tacaggaacc                                               20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gcgtctccaa ccagttccta                                               20

<210> SEQ ID NO 112
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
ccagcaccat gtcgatgac                                                19

<210> SEQ ID NO 113
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
aaggtgacaa gctccggt                                                 18

<210> SEQ ID NO 114
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 114
tctttgtctc cctgctgga                                                  19

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
cagaatatgg tgcactgtgc                                                 20

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
agtctatgaa gcccacctgt g                                               21

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
ctcaggccat gcactgttac                                                 20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
ggcaagtgtg agaacaaacc                                                 20

<210> SEQ ID NO 119
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
tgctcagagc tttcaacaac tactc                                           25

<210> SEQ ID NO 120
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 120
gaggctccag tgaattcgga                                             20

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
atggatgcta ccaaactgga t                                           21

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
gccactcctt ctgtgactcc                                             20

<210> SEQ ID NO 123
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
ttgtaccctg gcatacagtt tga                                         23

<210> SEQ ID NO 124
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
gttcccacgg cacttttc                                               18

<210> SEQ ID NO 125
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
tgtgctaaga ggtcctc                                                17

<210> SEQ ID NO 126
<211> LENGTH: 17
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 126
gaggacctct tagcaca                                                         17

<210> SEQ ID NO 127
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
agactcatcg ttgtacat                                                        18

<210> SEQ ID NO 128
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
atgtacaacg atgagtct                                                        18

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
accatgtcga tgaccatctt                                                      20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
aagatggtca tcgacatggt                                                      20

<210> SEQ ID NO 131
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
accatagtct tcaggtcag                                                       19

<210> SEQ ID NO 132
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 132
ctgacctgaa gactatggt                                                    19

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
ctagttcctc cagcgtctcc                                                   20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
ggagacgctg gaggaactag                                                   20

<210> SEQ ID NO 135
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
catctctgag aggtgtgtc                                                    19

<210> SEQ ID NO 136
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
gacacacctc tcagagatg                                                    19

<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
gacagagcgg taggtctg                                                     18

<210> SEQ ID NO 138
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 138
cagacctacc gctctgtc                                                     18

<210> SEQ ID NO 139
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
ctgattggag actccagg                                                     18

<210> SEQ ID NO 140
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
cctggagtct ccaatcag                                                     18

<210> SEQ ID NO 141
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
gatggacaat gtagtcaat                                                    19

<210> SEQ ID NO 142
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
attgactaca ttgtccatc                                                    19

<210> SEQ ID NO 143
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
tccagatcgt gagtggc                                                      17

<210> SEQ ID NO 144
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 144
gccactcacg atctgga                                                 17

<210> SEQ ID NO 145
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
cttgcttaat tcccagttc                                               19

<210> SEQ ID NO 146
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
gaactgggaa ttaagcaag                                               19

<210> SEQ ID NO 147
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
gtcagaacca gttcttc                                                 17

<210> SEQ ID NO 148
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
gaagaactgg ttctgac                                                 17

<210> SEQ ID NO 149
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
ggagcaatct tacagcttc                                               19

<210> SEQ ID NO 150
<211> LENGTH: 19

```
-continued

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
gaagctgtaa gattgctcc                                                    19
```